United States Patent
Cardinali et al.

(10) Patent No.: US 12,246,160 B2
(45) Date of Patent: Mar. 11, 2025

(54) LINEAR SHUTTLE PUMP FOR DRUG DELIVERY

(71) Applicant: Insulet Corporation, Acton, MA (US)

(72) Inventors: Steven Cardinali, Tewksbury, MA (US); Daniel Allis, Boxford, MA (US); Ian Hanson, Wayne, PA (US); Maureen McCaffrey, Arlington, MA (US); Chris Goetchius, San Diego, CA (US)

(73) Assignee: Insulet Corporation, Acton, MA (US)

( * ) Notice: Subject to any disclaimer, the term of this patent is extended or adjusted under 35 U.S.C. 154(b) by 652 days.

(21) Appl. No.: 17/552,407

(22) Filed: Dec. 16, 2021

(65) Prior Publication Data
US 2022/0105260 A1 Apr. 7, 2022

Related U.S. Application Data

(62) Division of application No. 16/433,481, filed on Jun. 6, 2019, now Pat. No. 11,229,736.
(Continued)

(51) Int. Cl.
*A61M 5/142* (2006.01)
*A61M 5/145* (2006.01)
*F04B 17/03* (2006.01)

(52) U.S. Cl.
CPC .... *A61M 5/14212* (2013.01); *A61M 5/14244* (2013.01); *A61M 5/1422* (2013.01); *A61M 5/145* (2013.01); *F04B 17/03* (2013.01)

(58) Field of Classification Search
CPC ............ A61M 5/14212; A61M 5/1422; A61M 5/14228; A61M 5/1424; A61M 5/14244;
(Continued)

(56) References Cited

U.S. PATENT DOCUMENTS

| | | | |
|---|---|---|---|
| 1,516,032 A * | 11/1924 | White | F04B 3/00 417/498 |
| 2,752,918 A | 7/1956 | Uytenbogaart et al. | |

(Continued)

FOREIGN PATENT DOCUMENTS

| | | |
|---|---|---|
| CN | 102498292 B | 7/2015 |
| CN | 204972511 U | 1/2016 |

(Continued)

OTHER PUBLICATIONS

International Search Report and Written Opinion for International Patent Application No. PCT/US2022/029012, mailed Aug. 19, 2022, 12 pages.

(Continued)

*Primary Examiner* — Quynh-Nhu H. Vu
(74) *Attorney, Agent, or Firm* — Goodwin Procter LLP

(57) ABSTRACT

Examples of fluid delivery drive system and/or pump system that creates a vacuum in a fluid line for drawing and expelling fluid are provided. The vacuum may be created by separating two components that are positioned within the sealed fluid line. Once the two components are separated and the fluid is contained within the volume created between the separated components, the two components may be shuttled within the sealed volume. The movement of the two components can seal off an inlet to the fluid line and then open a pathway to an outlet from the fluid line while ensuring the created volume between the two components is maintained constant. The two components can then be moved back together to expel the fluid from the created volume through the outlet for delivery, for example, to a patient. Other examples are disclosed and described.

20 Claims, 20 Drawing Sheets

Related U.S. Application Data

(60) Provisional application No. 62/681,165, filed on Jun. 6, 2018.

(58) Field of Classification Search
CPC ......... A61M 5/145; A61M 2005/14506; F04B 13/00; F04B 19/025; F04B 19/022; F04B 3/00; F04B 7/045
See application file for complete search history.

(56) References Cited

U.S. PATENT DOCUMENTS

| | | | | |
|---|---|---|---|---|
| 3,464,359 | A | * | 9/1969 | Johnson ............... A61M 5/142 604/152 |
| 3,695,788 | A | * | 10/1972 | Loomans ............... F04B 49/12 417/488 |
| 4,277,226 | A | | 7/1981 | Archibald |
| 4,991,743 | A | | 2/1991 | Walker |
| 5,628,309 | A | | 5/1997 | Brown |
| 5,639,220 | A | * | 6/1997 | Hayakawa ............ F04C 2/063 347/30 |
| 6,224,346 | B1 | * | 5/2001 | Denenburg ............ F04B 1/02 417/219 |
| 6,740,059 | B2 | | 5/2004 | Flaherty |
| 6,884,231 | B1 | * | 4/2005 | Walters ............. G01N 35/1016 604/82 |
| 7,137,964 | B2 | | 11/2006 | Flaherty |
| 8,267,921 | B2 | | 9/2012 | Yodfat et al. |
| 8,702,405 | B2 | * | 4/2014 | Verrilli ................. F04B 7/045 92/75 |
| 8,920,376 | B2 | | 12/2014 | Caffey et al. |
| 9,194,383 | B2 | * | 11/2015 | Knobel ................. F04B 15/02 |
| 9,903,351 | B2 | * | 2/2018 | Gros-D'Aillon ......... F04B 1/00 |
| 10,441,723 | B2 | | 10/2019 | Nazzaro |
| 10,881,800 | B2 | * | 1/2021 | Weibel .............. A61M 5/16827 |
| 2003/0055380 | A1 | | 3/2003 | Flaherty |
| 2003/0198558 | A1 | | 10/2003 | Nason et al. |
| 2009/0326472 | A1 | * | 12/2009 | Carter ............... A61M 5/14216 604/180 |
| 2011/0073620 | A1 | * | 3/2011 | Verrilli ................. F04B 13/00 222/325 |
| 2012/0172817 | A1 | | 7/2012 | Bruggemann et al. |
| 2012/0209207 | A1 | | 8/2012 | Gray et al. |
| 2013/0296792 | A1 | | 11/2013 | Cabiri |
| 2015/0051487 | A1 | | 2/2015 | Uber et al. |
| 2015/0290389 | A1 | * | 10/2015 | Nessel ...................... F04B 3/00 604/152 |
| 2016/0129190 | A1 | | 5/2016 | Haitsuka |
| 2016/0213851 | A1 | * | 7/2016 | Weibel ............... A61B 5/14532 |
| 2017/0290975 | A1 | | 10/2017 | Barmaimon et al. |
| 2020/0345931 | A1 | | 11/2020 | Gray et al. |

FOREIGN PATENT DOCUMENTS

| | | |
|---|---|---|
| CN | 105764543 B | 7/2016 |
| CN | 206175149 U | 5/2017 |
| CN | 107096091 A | 8/2017 |
| CN | 108472441 A | 8/2018 |
| DE | 102005040344 A1 | 3/2007 |
| EP | 1874390 B1 | 10/2014 |
| JP | 2009514580 A | 4/2009 |
| JP | 2017513577 A | 6/2017 |
| WO | 2010022069 A2 | 2/2010 |
| WO | 2010077279 A1 | 7/2010 |
| WO | 2011031458 A1 | 3/2011 |
| WO | 2013149186 A1 | 10/2013 |
| WO | 2014029416 A1 | 2/2014 |
| WO | 2014179774 A1 | 11/2014 |
| WO | 2015048791 A1 | 4/2015 |
| WO | 2021016452 A1 | 1/2021 |

OTHER PUBLICATIONS

International Search Report and Written Opinion for the International Patent Application No. PCT/US2021/055581, dated Feb. 8, 2022, 19 pages.

International Search Report and Written Opinion, Application No. PCT/US2022/016713, mailed Aug. 5, 2022, 19 pages.

International Search Report and Written Opinion for International Patent Application No. PCT/US2022/011356, dated Apr. 29, 2022, 19 pages.

* cited by examiner

LINEAR SHUTTLE PUMP FOR DRUG DELIVERY

CROSS REFERENCE TO RELATED APPLICATIONS

This application is a division of U.S. patent application Ser. No. 16/433,481, filed Jun. 6, 2019, which claims priority to Provisional Application No. 62/681,165, filed Jun. 6, 2018, the entire contents of which are incorporated herein by reference in their entirety.

BACKGROUND

Many wearable drug delivery devices include a reservoir for storing a liquid drug. A drive mechanism is operated to expel the stored liquid drug from the reservoir for delivery to a user. Often, the user is required to transfer the liquid drug from a vial or other container to the reservoir before it may be dispensed to the user.

Many conventional drive mechanisms, however, use a plunger to expel the liquid drug from the reservoir. Accordingly, the drive mechanism generally has a length equal to a length of the reservoir. When paired with a standardized pre-filled cartridge, these wearable drive mechanisms cause a length of the drug delivery devices to be significantly larger—for example, about twice the length of the cartridge. Increasing the size of the drug delivery devices to accommodate pre-filled cartridges and corresponding drive mechanisms leads to bulky devices that are uncomfortable for the user to wear.

It would be advantageous for drug delivery devices to include standardized pre-filled containers (e.g., 3 mL International Organization for Standardization cartridges) for storing and dispending the liquid drug, to obviate the need for the user to transfer the drug to the drug delivery device while also streamlining order fulfillment by supplying pre-filled drug delivery devices to the user. Accordingly, there is a need for a drive system for expelling a liquid drug from a reservoir, including a standardized, pre-filled cartridge, that reduces a size of a drug delivery device, allowing the size and form factor of the drug delivery device to remain compact and user-friendly.

SUMMARY

Disclosed is an example of a linear volume shuttle fluid pump. The example of the linear volume shuttle fluid pump includes a first grip component, a first plunger component, a second grip component, a second plunger component, and a pump chamber component. The first plunger component is coupled to the first grip component and the second plunger component is coupled to the second grip component. A portion of the first plunger component may be positioned in a fluid line of the pump chamber component and a portion of the second plunger component may be positioned in the fluid line of the pump chamber component. The pump chamber component may be positioned between the first and second grip components and may include an inlet pathway and an outlet pathway coupled to the fluid line, and the inlet pathway may be coupled to a reservoir storing a liquid drug, and the outlet pathway may be coupled to deliver the liquid drug.

Another example of a linear volume shuttle pump that includes a first closed-end needle, a second closed-end needle and a pump chamber is provided. The first closed-end needle has a first side port and the second closed-end needle having a second side port. The pump chamber component having a first end of the first closed-end needle and a first end of the second closed-end needle positioned within the pump chamber component, a second end of the first closed-end needle coupled to an outlet port coupled to deliver a liquid drug, and a second end of the second closed-end needle coupled to an inlet port coupled to a reservoir storing the liquid drug, wherein the pump chamber component includes a first seal, a second seal, a third seal, and a fourth seal.

A further example of a linear volume shuttle fluid pump is provided. The linear volume shuttle fluid pump includes a guide component, a pump chamber component, a piston positioned within the pump chamber component, wherein the pump chamber component is positioned around the piston. The piston nut is coupled to the piston, a piston crimp is coupled to the piston nut with a wire crimp coupled to the piston crimp. A shape memory alloy (SMA) wire is coupled to the wire crimp.

BRIEF DESCRIPTION OF DRAWINGS

These and other features of the disclosed subject matter will now be described with reference to the figures, wherein like reference numerals are used to refer to like elements throughout.

DETAILED DESCRIPTION

Various examples provide a drive system and/or pump system with the ability to extract a liquid drug from a reservoir and deliver the liquid drug to a patient without the need to press a plunger through the reservoir. As a result, a drug delivery device that contains the reservoir and the pump system may be made compact and more comfortable to wear for the patient.

Various examples provide a drive system and/or pump system that creates a vacuum in a fluid line that is coupled to a reservoir that stores a liquid drug or other fluid. The created vacuum pulls the liquid drug out of the reservoir to enable the liquid drug to be delivered to a patient. The vacuum may be created by separating two components—for example, two plunger components or closed-end needles—that are positioned within the sealed fluid line. Once the two components are separated and the liquid drug is contained within the volume created between the separated components, the two components may be shuttled within the sealed volume. The movement of the two components can seal off an inlet to the fluid line and then open a pathway to an outlet from the fluid line while ensuring the created volume between the two components is maintained constant. The two components can then be moved back together to expel the liquid drug from the created volume, through the outlet, and on to the patient. Other examples are disclosed and described.

Figure 1:
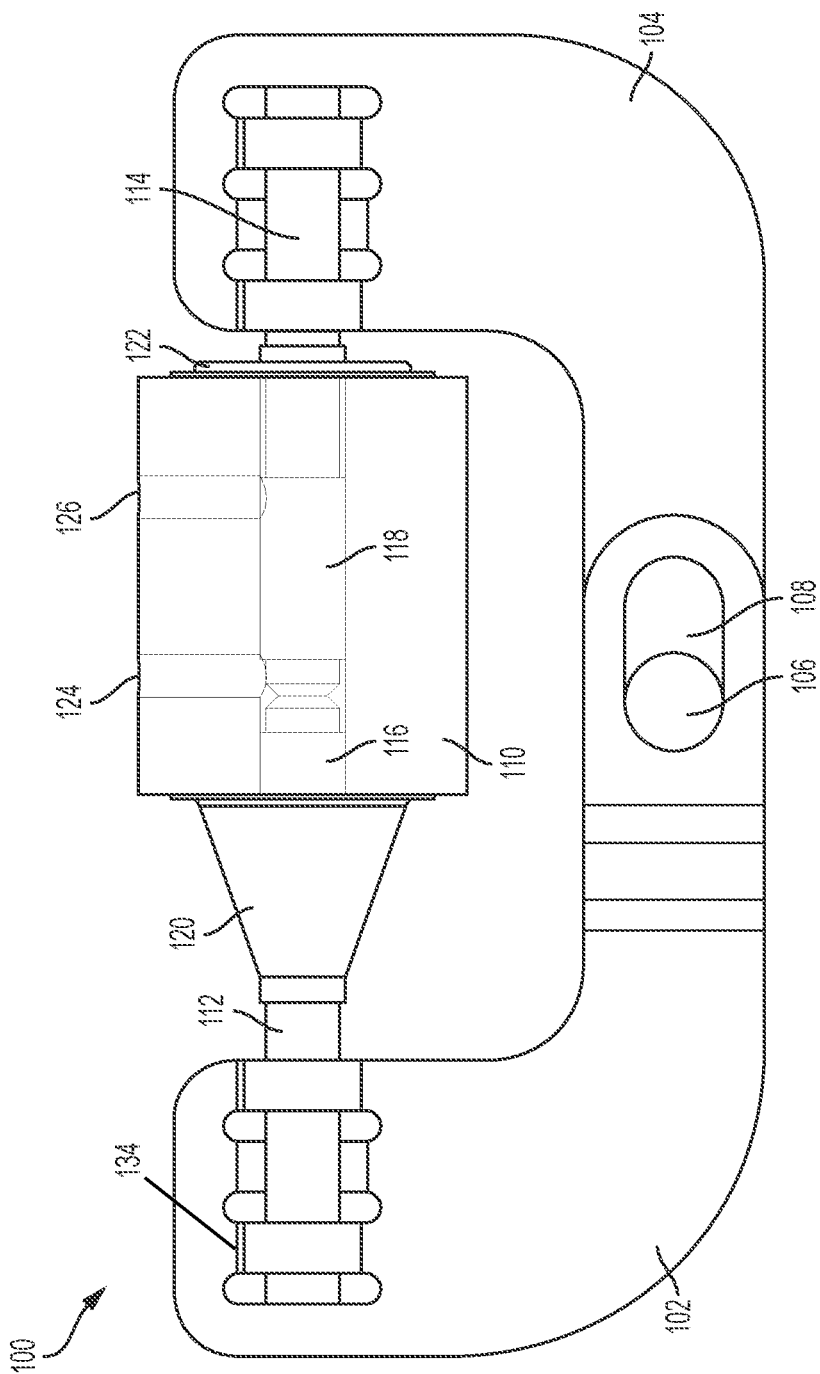
FIG. 1 illustrates an example of a linear volume shuttle fluid pump.

FIG. 1 illustrates an example of a linear volume shuttle fluid pump. As shown in the example of FIG. 1, the linear volume shuttle fluid pump 100 can include a first grip component 102 and a second grip component 104. The second grip component 104 can include a pin 106 that is positioned within an opening or slot 108 of the first grip component 102. The first and second grip components 102 and 104 may be coupled together by the pin 106 and the slot 108 as shown and further described herein.

The linear volume shuttle fluid pump 100 can further include a pump chamber component 110, a first plunger component 112, and a second plunger component 114. The first plunger component 112 may be coupled to the first grip component 102 via coupling 134. The second plunger component 114 may be coupled to the second grip component 104. The first and second plunger components 112 and 114 can each be positioned within the pump chamber component 110 (e.g., first ends of the first and second plunger components 112 and 114 may be positioned within the pump chamber component 110).

A first fluid seal 116 may be coupled to the first plunger component 112 (e.g., the first fluid seal 116 can cover a portion of the first plunger component 112) and is operable to seal the inlet pathway 124 based on a state of the linear volume shuttle pump 100. A second fluid seal 118 may be coupled to the second plunger component 114 (e.g., the second fluid seal 118 can cover a portion of the second plunger component 114) and is operable to seal the outlet pathway 126 based on a state of the linear volume shuttle pump 100. The first and second fluid seals 116 and 118 may be formed of a variety of materials including, for example, rubber.

A first microbe seal component 120 may be coupled to the first plunger component 112. As shown in FIG. 1, the first plunger component 112 may be positioned through the first microbe seal component 120. The first microbe seal component 120 may be pressed against a first end of the pump chamber component 110 and can form a first seal with the pump chamber component 110. A second microbe seal component 122 may be coupled to the second plunger component 114. As shown in FIG. 1, the second plunger component 114 may be positioned through the second microbe seal component 122. The second microbe seal component 122 may be pressed against a second end of the pump chamber component 110 and can form a second seal with the pump chamber component 110.

The pump chamber component 110 can include an inlet pathway or component 124 and an outlet pathway or component 126. A liquid or fluid can enter the pump chamber component 110 through the inlet 124 and can exit the pump chamber component 110 through the outlet pathway 126. The first and second plunger components 112 and 114 may be moved along an axis that is substantially perpendicular to the inlet and outlets 124 and 126 to draw a fluid into the pump chamber component 110 and to expel the fluid from the pump chamber component 110 as described herein. In various examples, the linear volume shuttle fluid pump 100 may be coupled to a reservoir (not shown in FIG. 1) that stores a fluid or liquid drug. For example, the inlet 124 may be coupled to the reservoir and the outlet pathway 126 may be coupled to a fluid path component (not shown in FIG. 1) that is coupled to a patient or user that is to receive the liquid drug stored in the reservoir.

In various examples, the first and second plunger components 112 and 114 are operable to move back and forth (relative to the depiction of the linear volume shuttle fluid pump 100 in FIG. 1) within an open area or fluid line (not shown in the example of FIG. 4) of the pump chamber component 110. The movements of the first and second plunger components 112 and 114 can create a vacuum within a portion of the pump chamber component 110 (e.g., within the fluid line of the pump chamber component 110). The created vacuum can pull a portion of the liquid drug out of the reservoir coupled to the inlet 124. In various examples, the vacuum may be created by separating the first and second plunger components 112 and 114 by a predetermined amount within the sealed fluid line of the pump chamber component 110. Once the first and second plunger components 112 and 114 are separated, an open area of created volume may be formed. The created vacuum can cause the liquid drug to be drawn into the created space/volume.

In various examples, after the liquid drug occupies the created volume formed from separating the first and second plunger components 112 and 114, the first and second plunger components 112 and 114 are moved to seal off the inlet 124 and to couple the liquid drug to the outlet pathway 126. When moving, the first and second plunger components 112 and 114 can maintain a constant volume of space between the first and second plunger components 112 and 114 that contains the liquid drug drawn from the reservoir. Once the liquid drug between the first and second plunger components 112 and 114 is coupled to the outlet pathway 126, the first and second plunger components 112 and 114 may be moved towards each other, thereby expelling the liquid drug from the pump chamber component 110 out of the outlet pathway 126 and to the patient.

The first and second grip components 102 and 104 (and, correspondingly, resulting movement of the first and second plunger components 112 and 114) may be actuated by a variety of mechanisms and/or actuators. In various examples, the first and second grip components 102 and 104 may be actuated independently or by the same actuator. In various examples, one of the first and second grip components 102 and 104 may be actuated by an actuator capable of producing reciprocating motion—for example, a piezo-electric-based actuator, a solenoid-based actuator, a Nitinol-based actuator, a spring-based actuator, a rotary motor with a gear drain, a direct current (DC) motor, or any combination thereof. The other of the first and second grip components 102 and 104 may be moved or translated using other features such as, for example, the pin 106 and slot 108. As a result, a desired effect of shuttling fluid (e.g., a liquid drug) may be achieved.

Figure 2:
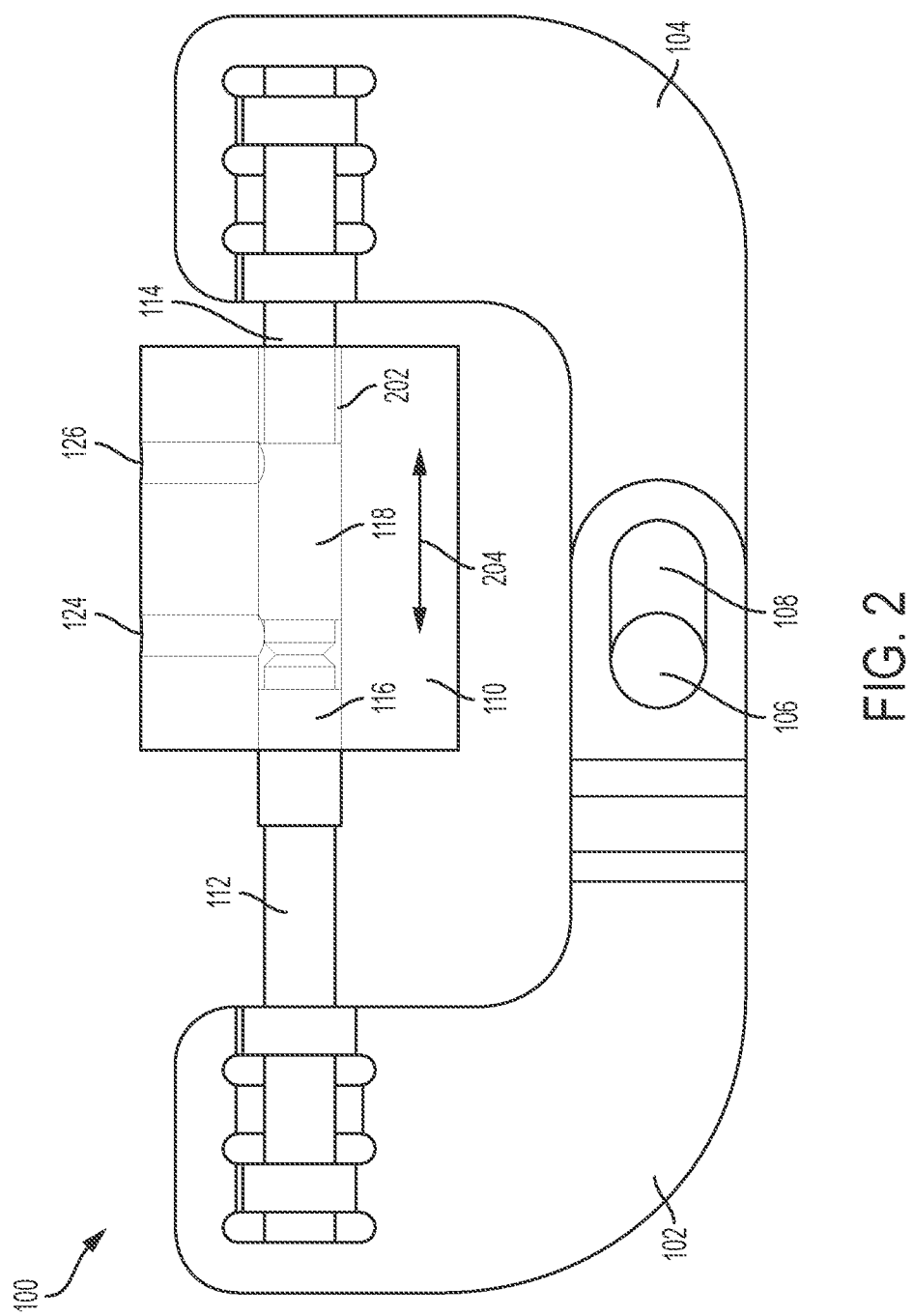
FIG. 2 illustrates another view of the example of the linear volume shuttle fluid pump depicted in FIG. 1.

FIG. 2 illustrates the linear volume shuttle fluid pump 100 depicted in FIG. 1 with the first and second microbe seals 120 and 122 removed to show the relative positioning and arrangement of the components of the linear volume shuttle fluid pump 100. As shown in FIG. 2, the first and second plunger components 112 and 114 can move within a fluid line or space 202 in directions indicated by directional indicator 204. For ease of reference, as shown in FIG. 2, the first and second plunger components 112 and 114 may be considered to move back and forth and/or left and right as shown by the directional indicator 204 within the fluid line or space 202, relative to the depiction of the linear volume shuttle fluid pump 100.

Figure 3:
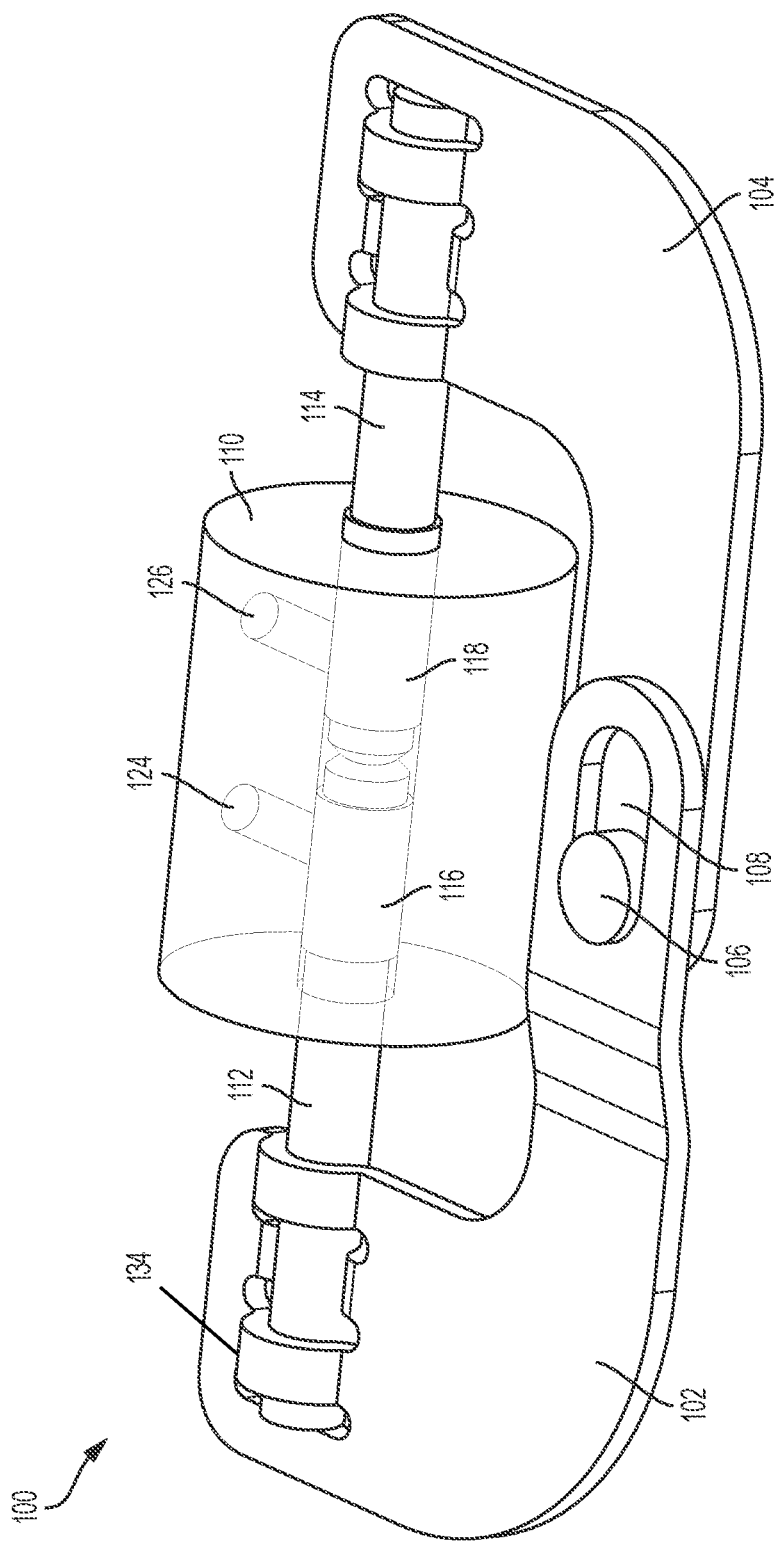
FIG. 3 illustrates a second view of the example of the linear volume shuttle fluid pump depicted in FIGS. 1 and 2.

FIG. 3 illustrates a second view of the linear volume shuttle fluid pump 100 depicted in FIG. 2. FIG. 3 provides an additional view of the linear volume shuttle fluid pump 100 to reveal the arrangement and positioning of the various constituent components of the linear volume shuttle fluid pump 100.

FIGS. 4-7 illustrate operation of the linear volume shuttle fluid pump 100. In particular, FIGS. 4-7 illustrate movement of various components of the linear volume shuttle fluid pump 100 to draw in a volume of liquid drug from an associated reservoir and to expel the liquid drug from the linear volume shuttle fluid pump 100 and on to the patient. FIGS. 4-7 illustrate the linear volume shuttle fluid pump 100 without the first and second microbe seal components 120 and 122 for simplicity.

Figure 4:
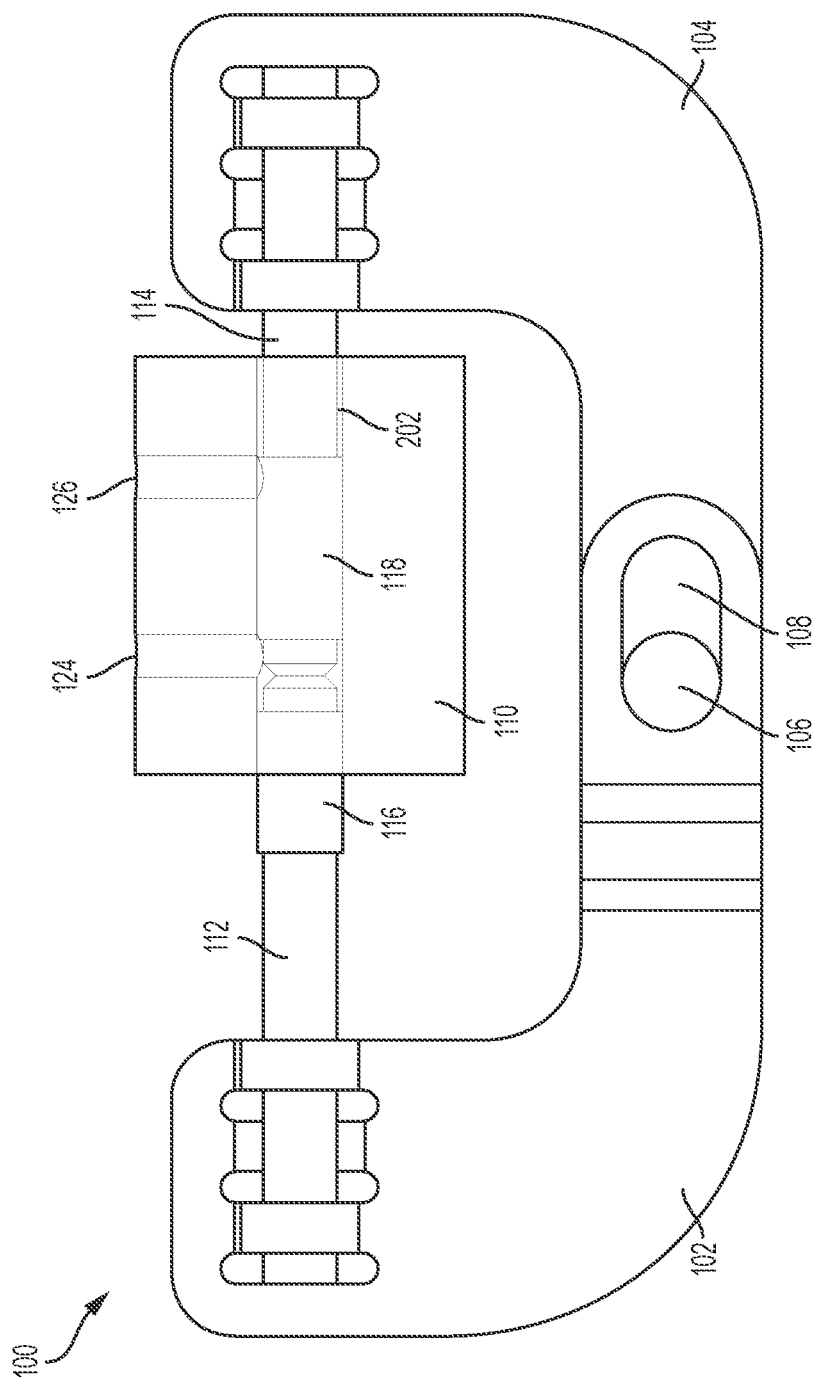
FIG. 4 illustrates the example linear volume shuttle fluid pump of FIG. 1 in an initial state of operation.

FIG. 4 illustrates the linear volume shuttle fluid pump 100 in an initial state (State 1) of operation. As shown in FIG. 4, the second grip component 104 is positioned against the first grip component 102 such that the pin 106 is pushed all the way to the left within the slot 108. The second fluid seal 118 is positioned adjacent to the outlet pathway 126 thereby sealing the fluid line 202 from the outlet pathway 126.

Figure 5:
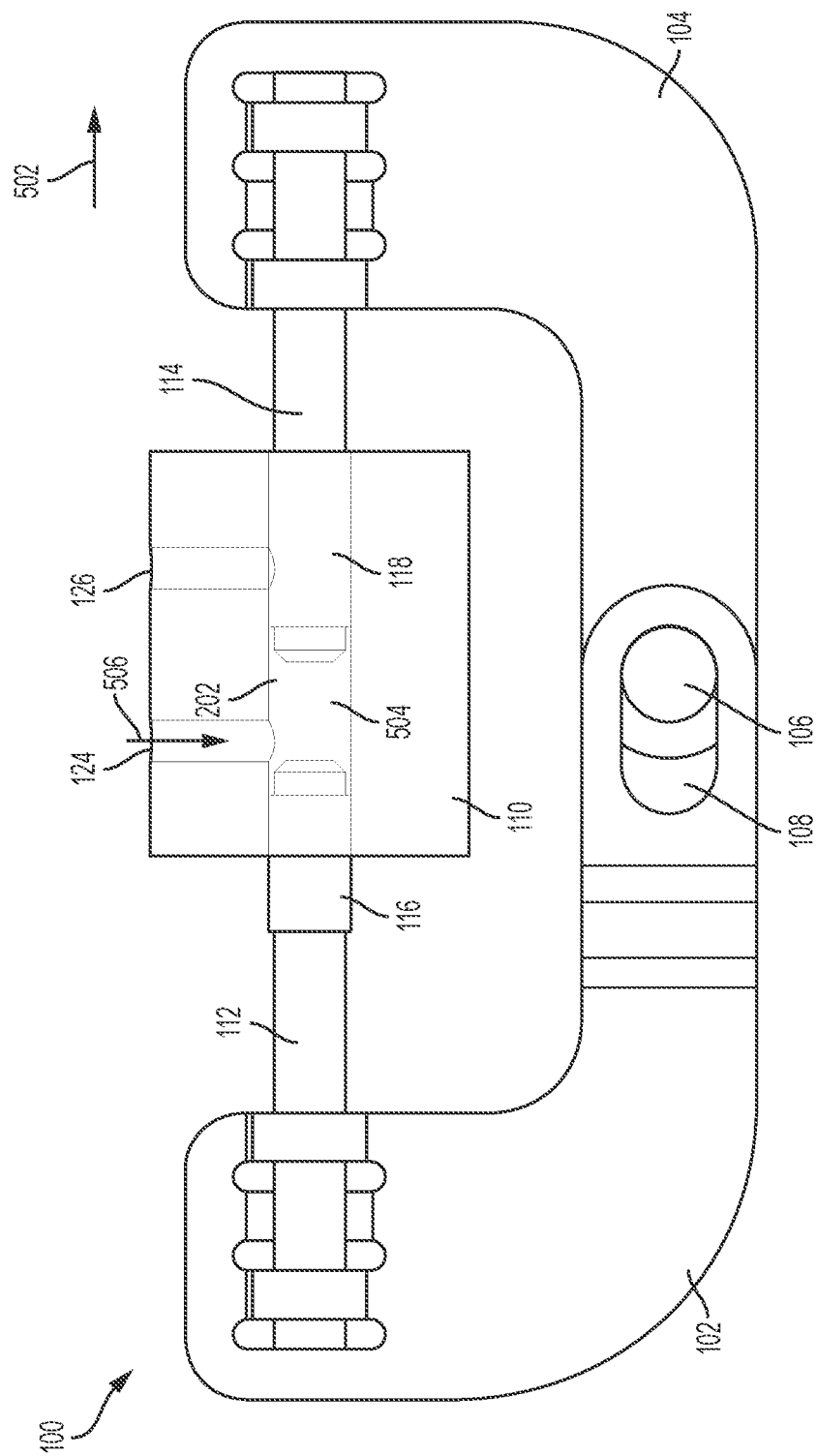
FIG. 5 illustrates the example linear volume shuttle fluid pump of FIG. 1 in a subsequent state of operation relative to the initial state example shown in FIG. 4.

FIG. 5 illustrates the linear volume shuttle fluid pump 100 in a subsequent state (State 2) of operation relative to the initial state of operation (State 1) shown in FIG. 4. In State 2, as shown in FIG. 5, the second grip component 104 is moved to the right in a direction 502. The first grip component 102 can remain in a fixed position. For example, the first grip component 102 may be held in place by another component (not shown for ease of illustration). In the example, the pin 106 moves to another position within the slot 108 at the far right of the slot 108 as the second grip component 104 moves in the direction 502. As the second plunger component 114 is coupled to the second grip component 104, the movement of the second grip component 104 in the direction 502 causes the second plunger component 114 to move in the direction 502. Accordingly, an opening or a created volume 504 is formed between the first plunger component 112 and second plunger component 114 within the pump chamber component 110 based on the fixed (or held) position of the first plunger component 112 and the movement of the second plunger component 114 in the direction 502.

The second fluid seal 118 can continue to seal the outlet pathway 126. The inlet 124 may be opened or exposed to the fluid line 202. The created volume 504 can draw in a portion of a liquid drug as indicated by directional indicator 506. Accordingly, the liquid drug flows in the direction indicated by directional indicator 506 into the created volume 504 from the inlet 124.

Figure 6:
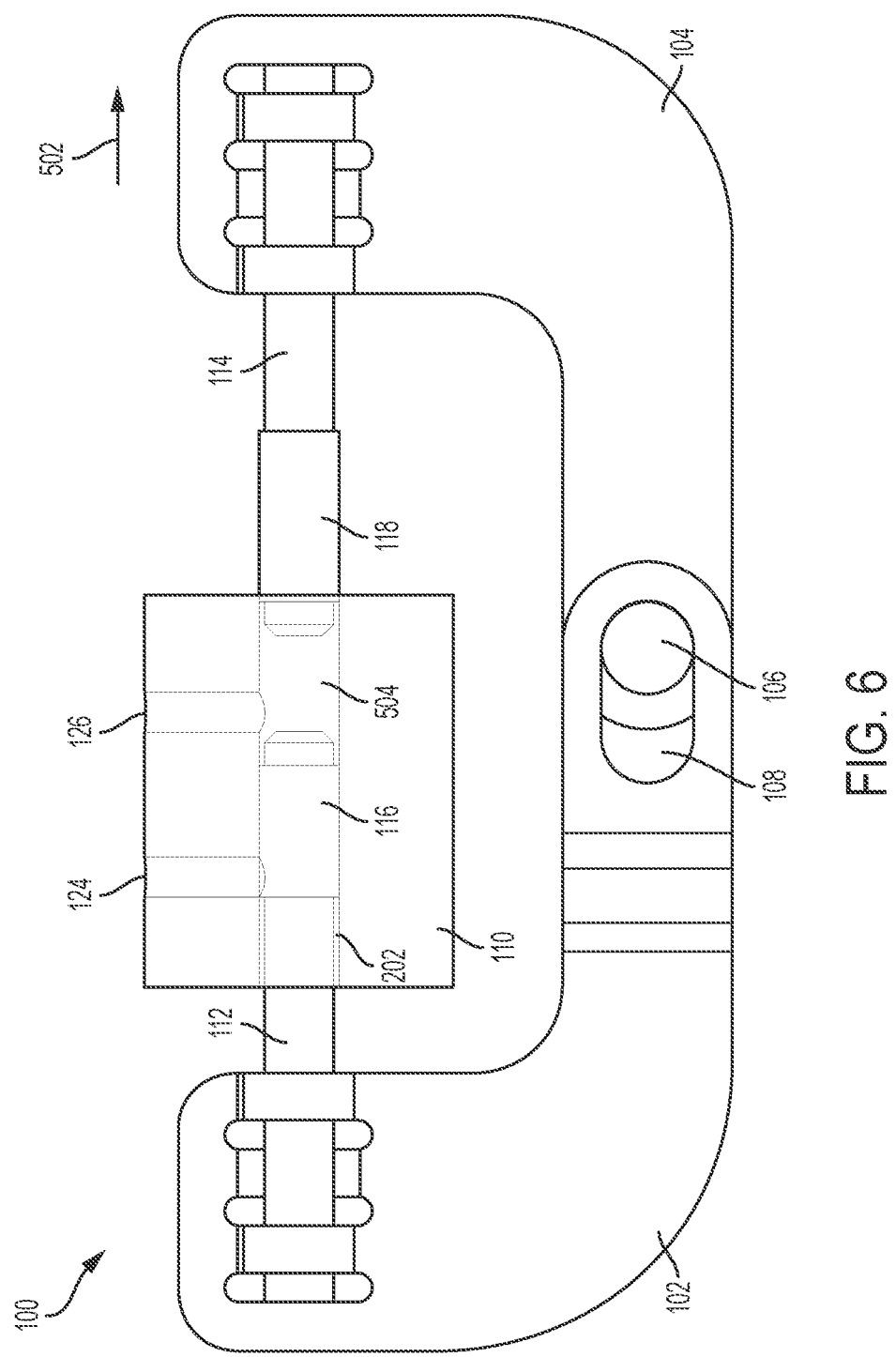
FIG. 6 illustrates the example linear volume shuttle fluid pump of FIG. 1 in a further state of operation relative to the state of operation shown in FIG. 5.

FIG. 6 illustrates the linear volume shuttle fluid pump 100 in a subsequent state of operation relative to the state of operation shown in FIG. 5. As shown in FIG. 6, the second grip component 104 is continued to be moved in the direction 502. As a result, the second plunger component 114 is also moved further in the direction 502. Since the pin 106 was positioned all the way to the far right in the slot 108 in the prior operational state (as shown in FIG. 5), the further movement of the second grip component 104 in the direction 502 causes the first grip component 102, and consequently the first plunger component 112, to move in the direction 502.

The movement of the first and second grip components 102 and 104 and the first and second plunger components 112 and 114 in the direction 502 causes the created volume 504 to also move in the direction 502 within the fluid line 202. As shown in FIG. 6, the inlet 124 is now sealed by the first fluid seal 116 and the outlet pathway 126 is no longer sealed by the second fluid seal 118. The created volume 504 containing the liquid drug may be coupled to the outlet pathway 126. The movement of the first and second grip components 102 and 104 can ensure that a size of the created volume 504 remains the same in the operational states shown in FIGS. 5 and 6.

Figure 7:
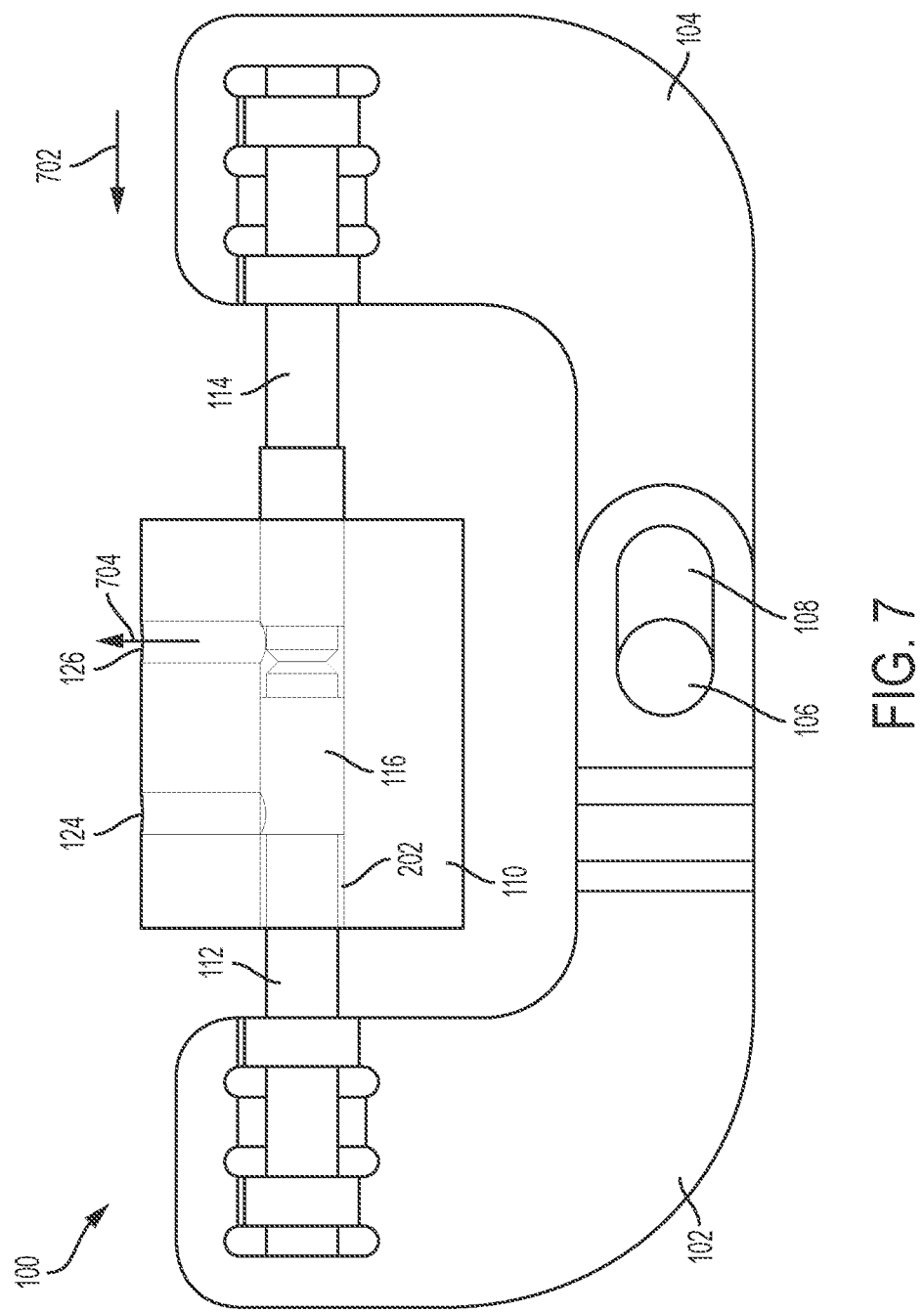
FIG. 7 illustrates the example linear volume shuttle fluid pump of FIG. 1 in yet another state of operation relative to the state of operation shown in FIG. 6.

FIG. 7 illustrates the linear volume shuttle fluid pump 100 in a subsequent state of operation relative to the state of operation shown in FIG. 6. As shown in FIG. 7, the second grip component 104 is moved in the direction 702 (e.g., opposite to the direction 502). The movement of the second grip component 104 in the direction 702 expels the fluid from the pump chamber component 110 through the outlet pathway 126 as indicated by flow direction 704. Accordingly, the liquid drug previously positioned in the pump chamber component 110 may be provided to the patient.

As further shown in FIG. 7, the movement of the second grip component 104 in the direction 702 causes the pin 106 to move in the direction 702 and to be positioned to the far left of the slot 108. The first grip component 102 and the first plunger component 112 can remain stationary or in a fixed position. After expelling the liquid drug, the inlet 124 and the outlet pathway 126 are sealed from the fluid line 202 of the pump chamber component 110.

Once the pin 106 is positioned as shown in FIG. 7, the second grip component 104 may be moved further in the direction 702 to push the first grip component 102 and the first plunger component 112 in the direction 702. When pushed in the direction 702 far enough, the first and second grip components 102 and 104 and the first and second plunger components 112 and 114 may be re-positioned as shown in FIG. 4. In this way, the linear volume shuttle fluid pump 100 may be reset to begin another cycle of creating a volume, drawing in a fluid, and then expelling the fluid.

Figure 8:
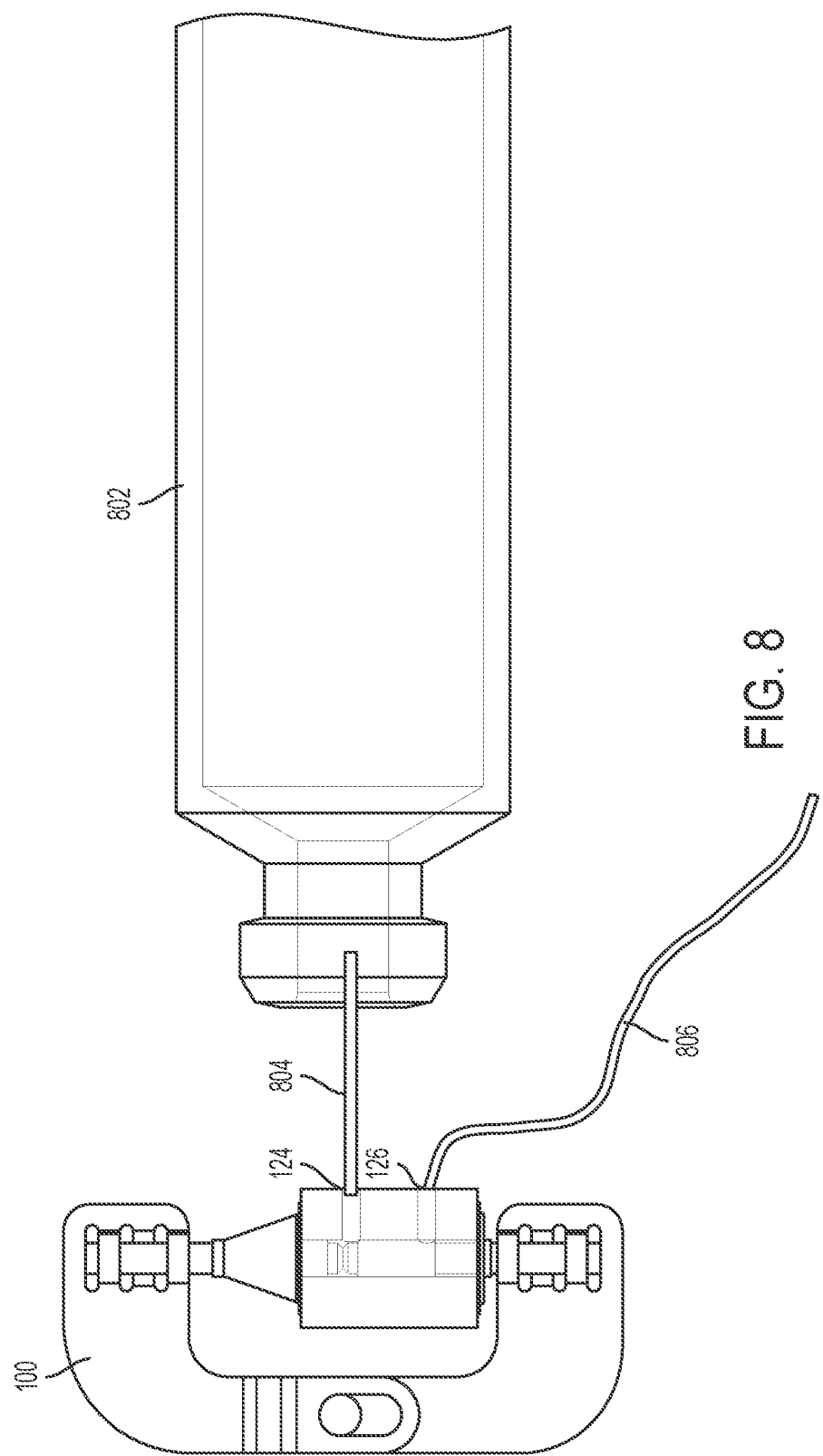
FIG. 8 illustrates the example linear volume shuttle fluid pump of FIG. 1 coupled to an example of a reservoir.

FIG. 8 illustrates the linear volume shuttle fluid pump 100 coupled to an example of a reservoir. As shown in FIG. 8, the example reservoir 802 is shown as a cartridge—for example, an International Organization for Standardization (ISO) drug cartridge—but is not so limited. The reservoir 802 may be any type of reservoir including a flexible reservoir, a rigid plastic reservoir, or a glass reservoir. Further, the reservoir 802 can have any desired shape, size, and/or form factor.

FIG. 8 illustrates an exemplary arrangement of the linear volume shuttle fluid pump 100 in relation to the reservoir 802. As shown, the inlet 124 may be coupled to the reservoir 802 by a first fluid path component 804. The first fluid path component 804 may be of any size and shape and may be made from any material. The first fluid path component 804 can allow fluid, such as a liquid drug, from the reservoir 802 to be transferred to the pump chamber component 110 through the inlet pathway 124.

As further shown in FIG. 8, the outlet pathway 126 may be coupled to a second fluid path component 806. The second fluid path component 806 may be of any size and shape and may be made from any material. The second fluid component 806 may be coupled to a patient and can allow fluid expelled from the pump chamber component 110 to be provided to the patient through the outlet pathway 126. The first and second fluid components 804 and 806, respectively, may be rigid or flexible.

Figure 9:
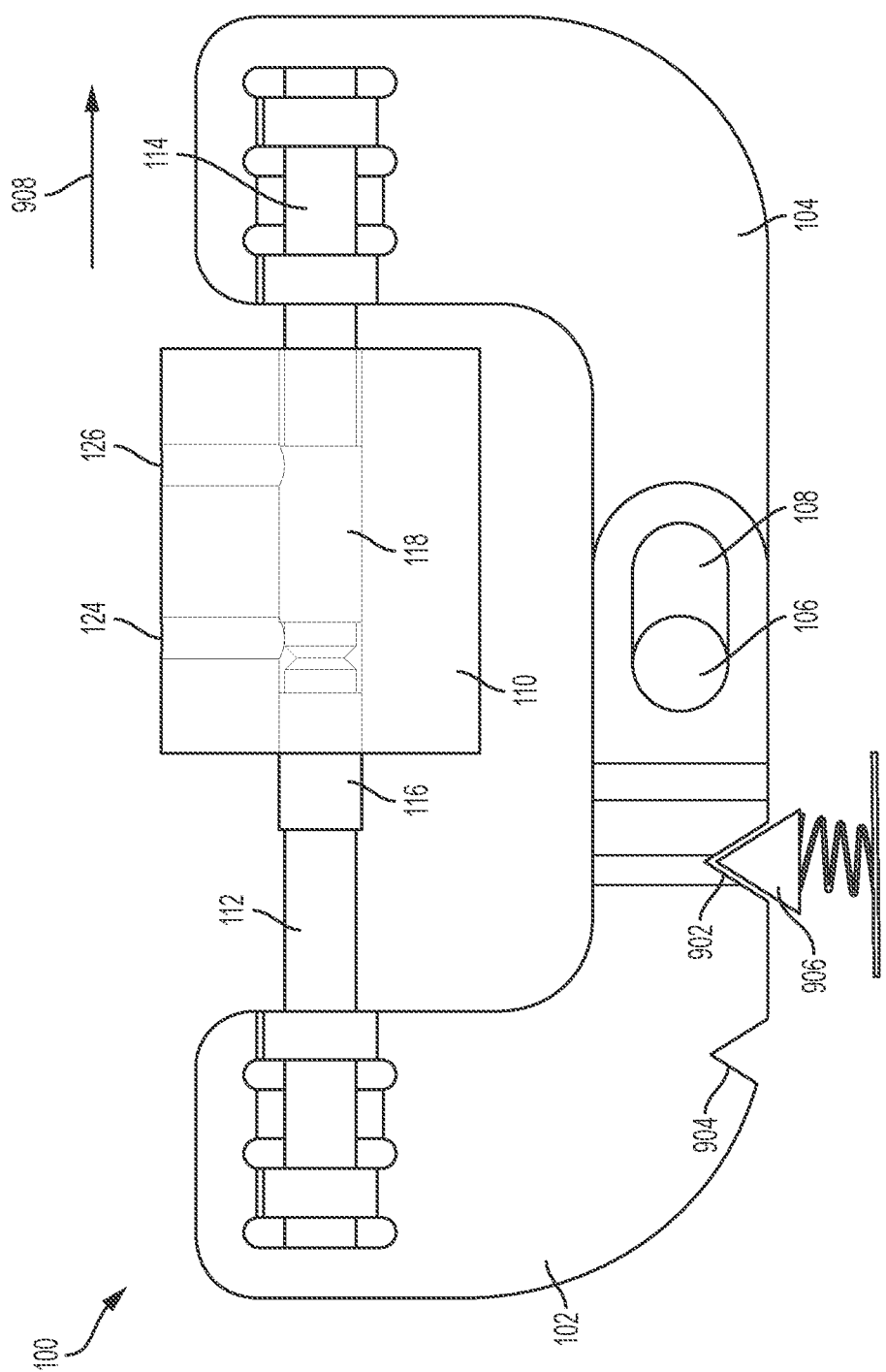
FIG. 9 illustrates another example of a linear volume shuttle fluid pump having a first detent and a second detent.

FIG. 9 illustrates the linear volume shuttle fluid pump 100 having a first detent 902 and a second detent 904. The first and second detents 902 and 904 may be positioned on the first grip component 102. An associated detent component 906 is shown in relation to the first and second detents 902 and 904. The associated detent component 906 may be an anchored or stationary component that may be coupled to the first and second detents 902 and 904.

The first and second detents 902 and 904 can help add additional frictional forces to restrict movement of the first grip component 102 prior to a desired time. For example, FIG. 9 shows that the first detent 902 can help restrict movement of the first grip component 102 in the direction 908 until the pin 106 fully moves to the far-right side of the slot 108. In this way, the first detent 902 (e.g., in conjunction with the associated detent component 906) can prevent premature movement of the first grip component 102 in the direction 908.

Figure 10:
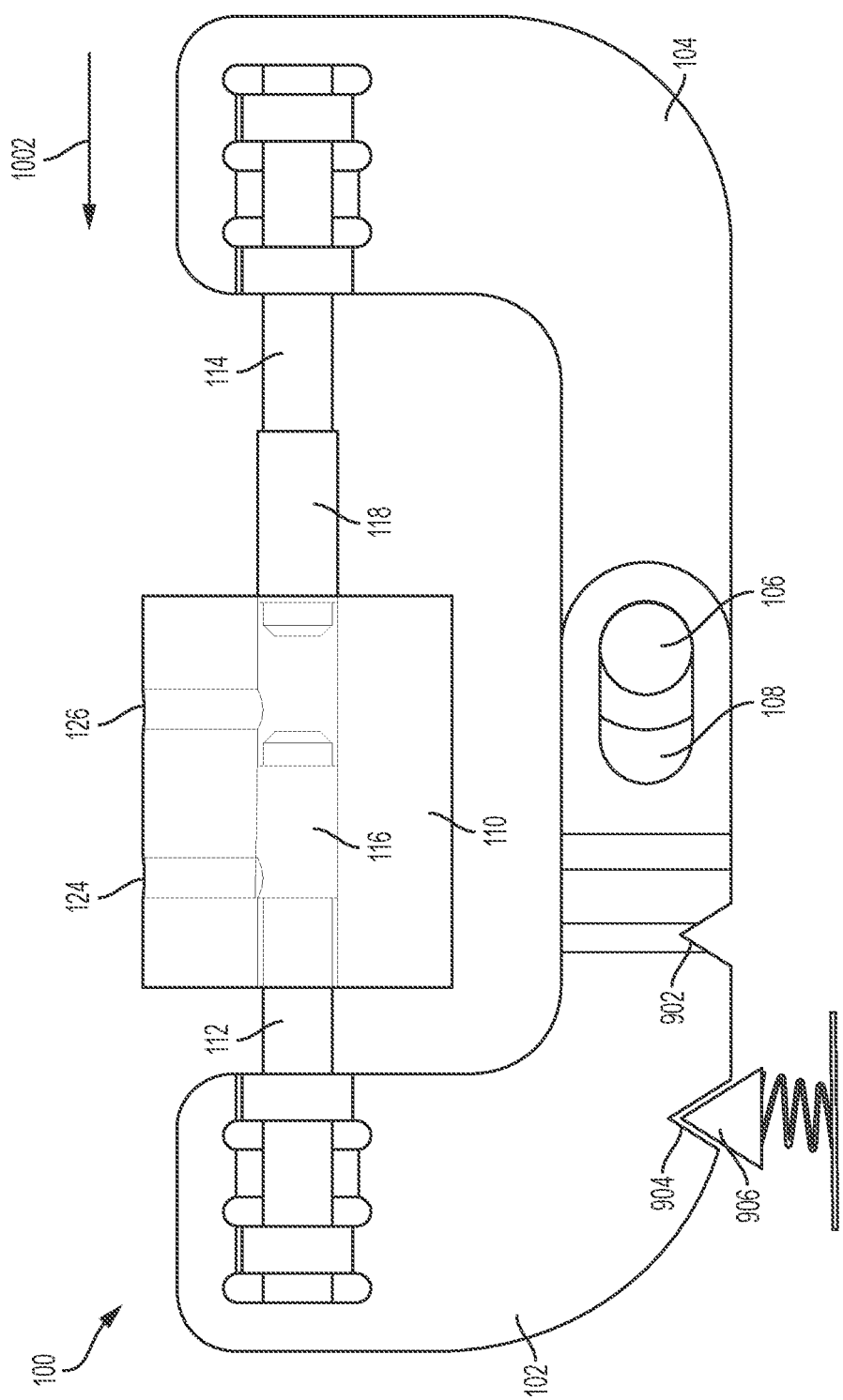
FIG. 10 illustrates a further operation of the example of FIG. 9.

FIG. 10 illustrates operation of the second detent 904. Specifically, the second detent 904 (e.g., in conjunction with the associated detent component 906) can prevent premature movement of the first grip component 102 in a direction 1002. For example, the second detent 904 can restrict movement of the first grip component 102 until the second grip component 104 has moved far enough in the direction 1002 to cause the pin 106 to be all the way left in the slot 108. This can aid the expelling of the fluid from the pump chamber component 110 by preventing movement of the first grip component 102 in the direction 1002 prior to a desired time.

Figure 11:
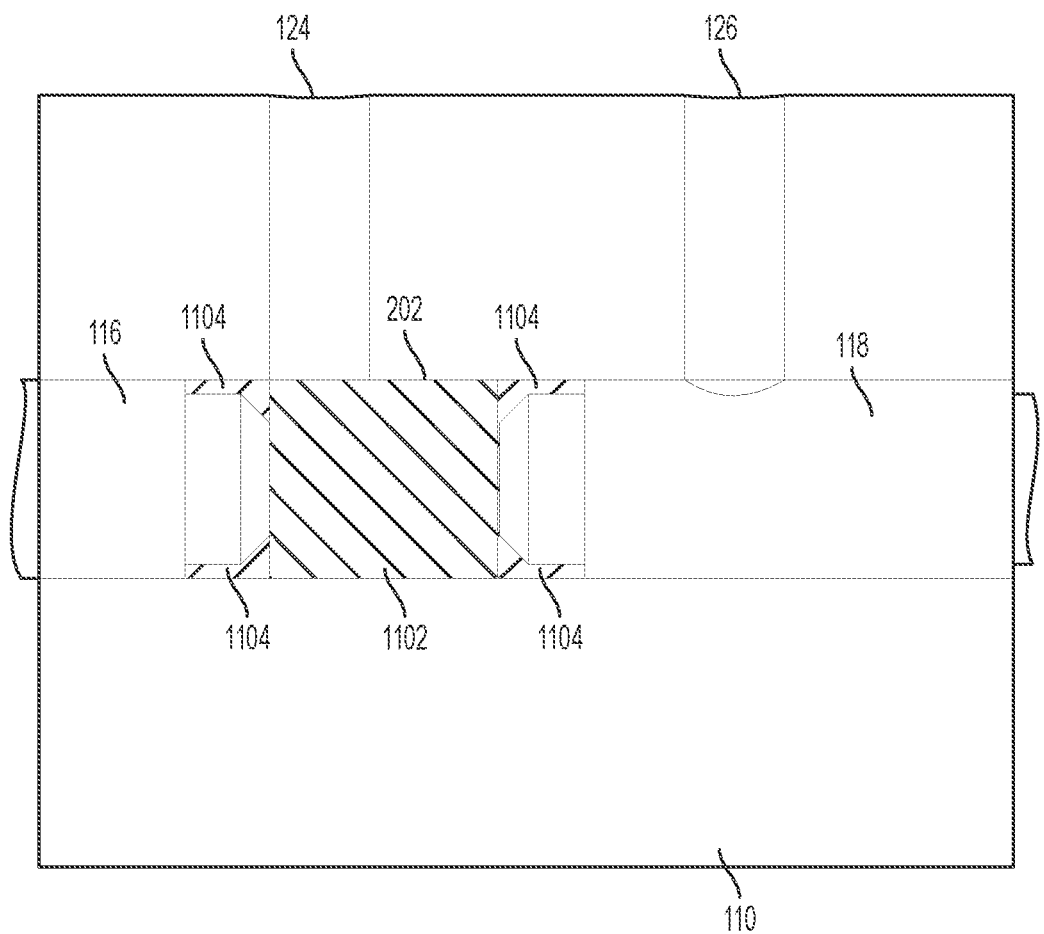
FIG. 11 illustrates a close-up view of an example of pump chamber component from the linear volume shuttle pump of FIG. 1.

FIG. 11 illustrates a close-up view of the pump chamber component 110. As shown in FIG. 11, the first and second plunger components 112 and 114 are separated from one another within the fluid line 202. A first portion 1102 can represent a volume created by moving the first and second plunger components 112 and 114 apart. This first portion 1102 can represent the amount (e.g., volume) of liquid drug that may be dispensed to the patient.

A second portion 1104 can represent a "dead" volume. The dead volume may contain a portion of the liquid drug that will not be delivered. The second portion 1104 can represent volume created by nominal gaps between the constituent components of the linear volume shuttle fluid pump 100. The first portion 1102 may be created by the linear volume shuttle fluid pump 100 during each cycle of operation and can help achieve a dose accuracy of approximately 5%.

In various examples, the linear volume shuttle fluid pump 100 may be modified to not include rubber seals. In various examples, the linear volume shuttle fluid pump 100 may be modified to have each plunger component driven independently (e.g., out of phase). In various examples, the linear volume shuttle fluid pump 100 may be modified to provide rotational movement of the plunger components instead of linear movement to expose or seal off the inlet and outlet ports. In various examples, the linear volume shuttle fluid pump 100 may be modified to include a cammed level to move each grip component independently.

Figure 12:
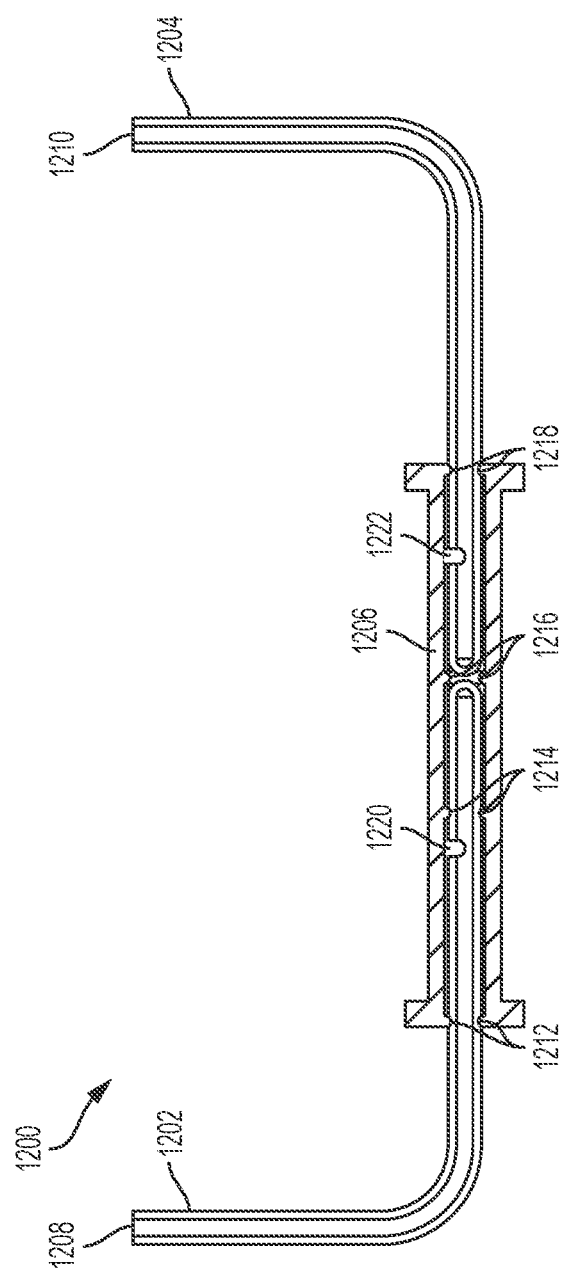
FIG. 12 illustrates an example of a linear volume shuttle pump with closed-end needles.

FIG. 12 illustrates an example of a linear shuttle pump with closed-end needles. As shown in FIG. 12, the linear shuttle pump 1200 can include a first closed-end needle 1202, a second closed-end needle 1204, and a pump chamber component 1206. The first and second closed-end needles 1202 and 1204, respectively, can each be hollow core pistons. The pump chamber component 1206 may be a flexible cannula and may be formed of a soft plastic material.

A first end of the first closed-end needle 1202 may be an outlet port 1208. The outlet port 1208 may be coupled to a patient and/or a fluid path component that is coupled to a patient. A second end of the first closed-end needle 1202 may be positioned inside of the pump chamber component 1206. A first end of the second closed-end needle 1204 may be an inlet port 1210. The inlet port 1210 may be coupled to a reservoir storing a liquid drug. A second end of the second closed-end needle 1204 may be positioned inside of the pump chamber component 1206. The first and second closed-end needles 1202 and 1204 may be of any size, shape, or length and are not limited to the arrangement shown in FIG. 12.

The pump chamber component 1206 can include a first seal 1212, a second seal 1214, a third seal 1216, and a fourth seal 1218. In the example, the first seal 1212 and the fourth seal 1218 may prevent fluid (e.g., a liquid drug) from leaking from the pump chamber component 1206 by sealing respective ends of the pump chamber component. The second seal 1214 may seal the outlet 1208 from leaking fluid based upon a position of the first closed-end needle 1202 with respect to the second closed-end needle 1204, and the third 1216 seal may seal and prevent fluid from leaking from the inlet based on a different position of the first closed-end needle 1202 with respect to the second closed-end needle 1204. The first closed-end needle 1202 can include a first port 1220 (e.g., side port). The second closed-end needle 1204 can also include a second port 1222 (e.g., side port). The first port 1220 may be coupled to (e.g., in fluid communication with) the outlet 1208 (not shown in FIG. 13 for simplicity). The second port 1222 may be coupled to (e.g., in fluid communication with) the inlet port 1210 (not shown in FIG. 13 for simplicity).

Similar to the linear volume shuttle fluid pump 100 (e.g., the first and second grip components 102/104 and the first and second plunger components 112/114), the first and second closed-end needles 1202 and 1204 may be operable to move back and forth within the pump chamber component 1206 to draw fluid out of the reservoir and into the pump chamber component 1206. Further, in the example, the movement of the first and second closed-end needles 1202 and 1204 expels the fluid out of the pump chamber component 1206 for delivery of the fluid (e.g., a liquid drug) to, for example, a patient. Accordingly, the linear shuttle pump 1200 may be operated similarly to the linear volume shuttle fluid pump 100 to provide the same functions and benefits while providing an arrangement of components that provides tight tolerances and reduced friction.

The first and second closed-end needles 1202 and 1204 may be actuated separately (e.g., with independent actuators) or with the same actuator, for example, using any of the actuators or techniques disclosed herein in relation to the linear volume shuttle fluid pump 100.

Figure 13:
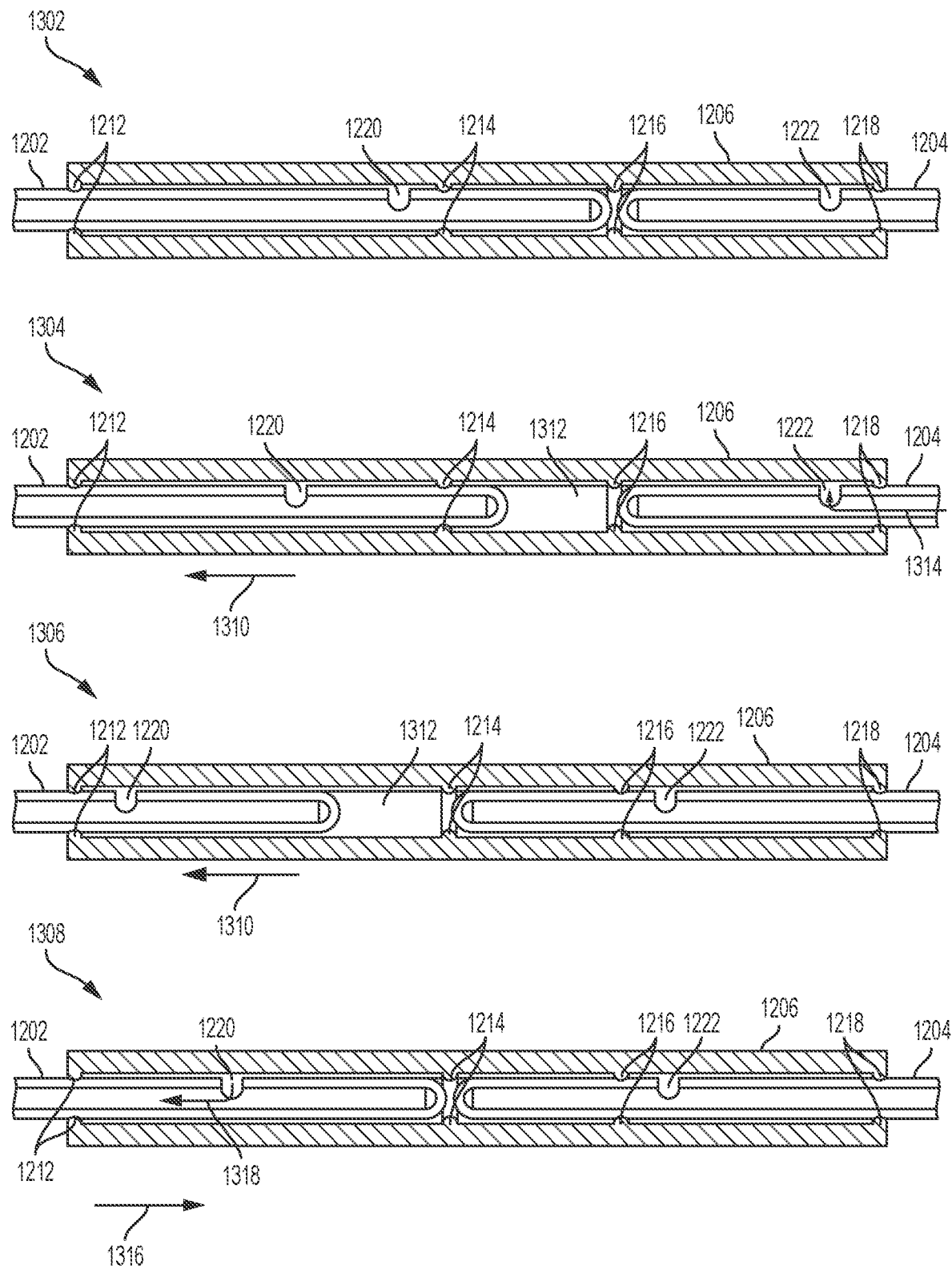
FIG. 13 illustrates an example operation of the example linear volume shuttle pump of FIG. 12.

FIG. 13 illustrates operation of the linear shuttle pump 1200. Specifically, FIG. 13 shows a sequence of operations for moving the first and second closed-end needles 1202 and 1204, respectively, to draw a portion of a liquid drug out of a reservoir and to then expel the liquid drug from the linear shuttle pump 1200 to the outlet 1208 for delivery via a coupling, such as a needle or cannula (not shown), to the patient.

For example, at 1302, the linear shuttle pump 1200 is shown in an initial stage of operation and is operable to perform different functions. For example, at 1304, the first closed-end needle 1202 is moved in a direction 1310 while the second closed-end needle 1204 is held in a fixed position. This movement creates an opening or drug chamber 1312 positioned between the second ends of the first and second closed-end needles 1202 and 1204. The outlet port 1208 is sealed off from the drug chamber 1312. The opening or drug chamber 1312 is a volume for holding a liquid drug received via the inlet port. As the first closed-end needle 1202 is moved in the direction 1310, a portion of a liquid drug from a reservoir flows into the inlet port 1210, through the second port 1222, and on into the created drug chamber 1312 (shown by arrow 1314).

At 1306, the first and second closed-end needles 1202 and 1204 both move in the direction 1310. The movement of the second closed-end needle 1204 in the direction 1310 can seal off the second port 1222 from the drug chamber 1312. Further, the movement of the first closed-end needle 1202 in the direction 1310 can open the first port 1220 to the drug chamber 1312. The volume of the drug chamber 1312 can remain approximately the same as the first and second closed-end needles 1202 and 1204 are moved together in the direction 1310.

At 1308, the first closed-end needle 1202 is moved in a direction 1316 (e.g., opposite to the direction 1310) as the position of the second closed-end needle 1204 is held fixed. This movement displaces the liquid drug from the drug chamber 1312 and pushes it out of the first port 1220 and on out to the outlet 1208 (shown by arrow 1318). The second closed-end needle 1204 can then also be moved in the direction 1316 to reset the linear shuttle pump 1200 (and positioning of the first and second closed-end needles 1202 and 1204) to the state shown in 1302.

In comparison to the linear volume shuttle fluid pump 100, the linear shuttle pump 1200 (e.g., by using closed-end needles with side ports) can remove the need for additional fluid paths and/or connections for forming the inlet and outlet valves of the pump and can reduce the risk of abrasion from sliding plungers along any inlet or outlet ports.

Figure 14:
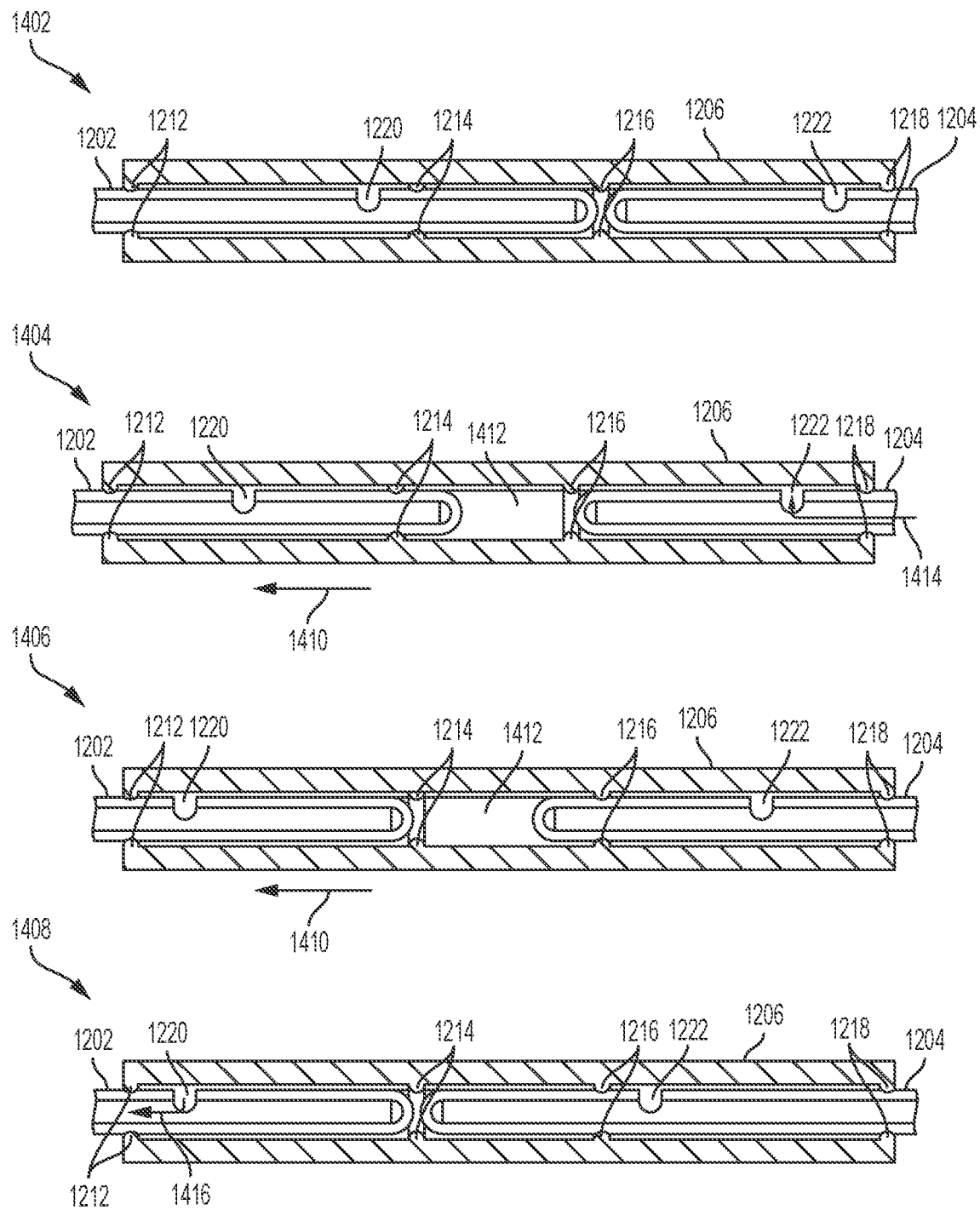
FIG. 14 illustrates an alternative operation of the example linear volume shuttle pump of FIG. 12.

FIG. 14 illustrates an alternative operation of the linear shuttle pump 1200. Specifically, FIG. 14 shows a sequence of operations for moving the first and second closed-end needles 1202 and 1204 to draw a portion of a liquid drug out of a reservoir and to then expel the liquid drug from the linear shuttle pump 1200 for delivery to the patient. The alternative operation can allow for shorter sealed lengths and shorter movement of the components of the linear shuttle pump 1200.

For example, at 1402, the linear shuttle pump 1200 is shown in an initial stage of operation. At 1404, the first closed-end needle 1202 is moved in a direction 1410 while the second closed-end needle 1204 is held in a fixed position. This movement creates an opening or drug chamber 1412 between the second ends of the first and second closed-end needles 1202 and 1204. The outlet port 1208 is sealed off from the drug chamber 1412. As the first closed-end needle 1202 is moved in the direction 1410, a portion of a liquid drug from a reservoir flows into the inlet port 1210, through the second port 1222, and on into the created drug chamber 1412 (shown by arrow 1414).

At 1406, the first and second closed-end needles 1202 and 1204 both move in the direction 1410. The movement of the second closed-end needle 1204 in the direction 1410 can seal off the second port 1222 from the drug chamber 1412. Further, the movement of the first closed-end needle 1202 in the direction 1410 can open the first port 1220 to the drug chamber 1412. The volume of the drug chamber 1412 can remain approximately the same as the first and second closed-end needles 1202 and 1204 are moved together in the direction 1410.

At 1408, the first closed-end needle 1202 may be held in a fixed position as the second closed-end needle 1204 is continued to be moved in the direction 1410. This movement displaces the liquid drug from the drug chamber 1412 and pushes it out of the first port 1220 and on out to the outlet 1208 (shown by arrow 1416).

The first and second closed-end needle 1202 and 1204 can then both be moved in the direction 1410 to reset the linear shuttle pump 1200 (and positioning of the first and second closed-end needles 1202 and 1204) to the state shown in 1402. The sequence 1402-1408 can provide for a shorter stroke for the linear shuttle pump 1200 in comparison to the sequence 1302-1308 shown in FIG. 13.

Figure 15:
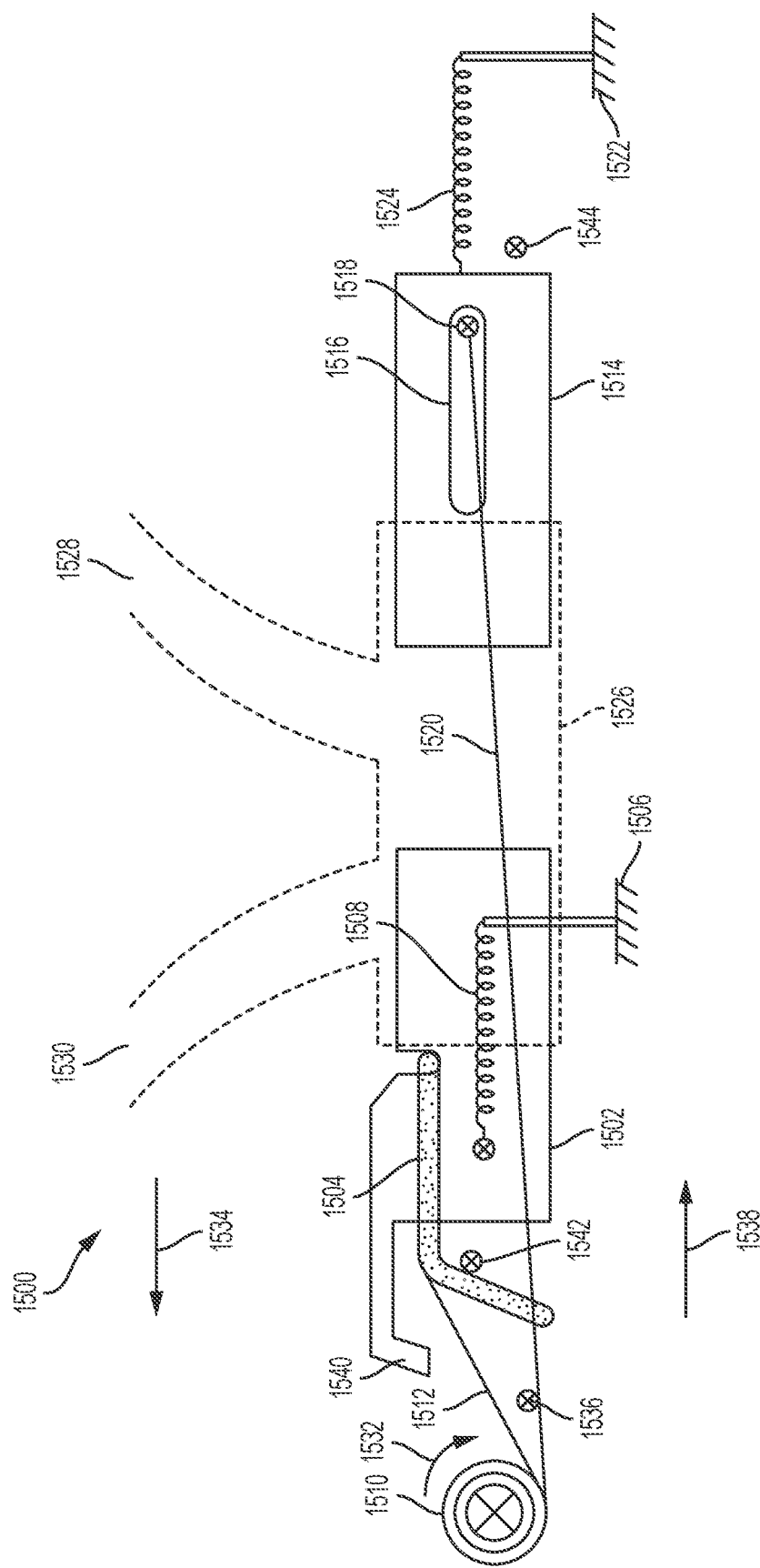
FIG. 15 illustrates an example of an actuator system usable with another example of a linear volume shuttle pump.

FIG. 15 illustrates an actuator system 1500. The actuator system 1500 may be used in conjunction with the with the linear shuttle pump 1200 to implement the sequence 1302-1308 shown in FIG. 13. The actuator system 1500 can include a first component 1502 and a rotatable bar or arm 1504. The first component 1502 can represent the first closed-end needle 1202 or can represent a part or component coupled to the first closed-end needle 1202. The first component 1502 may be coupled to a first anchor 1506 by a first spring 1508. The bar 1504 may be coupled to the first component 1502. The bar 1504 may be connected to a rotating component 1510 by a first shape memory alloy (SMA) wire (e.g., a Nitinol wire) 1512.

The actuator system 1500 can further include a second component 1514. The second component 1514 can represent the second closed-end needle 1204 or can represent a part or component coupled to the second closed-end needle 1204. The second component 1514 can include a slot 1516. A pin 1518 may be positioned within the slot 1516. The pin 1518 may be coupled to the rotating component 1510 by a second SMA wire (e.g., a Nitinol wire) 1520. The second component 1514 may be coupled to a second anchor 1522 by a second spring 1524.

For reference, a pump chamber component 1526 is shown in phantom along with an inlet port or pathway 1528 and an outlet port or pathway 1530. The first component 1502 may be considered to be a first piston and the second component 1514 may be considered to be a second piston.

During operation, the rotating component 1510 can rotate in a first direction 1532 (e.g., clockwise as shown in FIG. 15). The rotating component 1510 can rotate in the first direction 1532 based on actuation of the wire 1512 or may be caused to rotate through another mechanism. Overall, the wire 1512 can pull the bar 1504 in a direction 1534. Based on the coupling of the bar 1504 to the first component 1502, the first component 1502 is also pulled in the direction 1534.

The first component 1502 and the bar 1504 may be pulled in the direction 1534 until the bar 1504 engages a stop 1536. The stop 1536 can engage the bar 1504 and can cause it to rotate and to disengage or de-couple from the first component 1502, thereby causing the first component 1502 from being pulled further in the direction 1534.

Also, during operation, the wire 1520 can pull the pin 1518 in the direction 1534 within the slot 1516. Once the pin reaches the far-left end of the slot 1516, the pin 1518 can cause the second component 1514 to move in the direction 1534. Prior to the pin 1518 reaching the far-left end of the slot 1516, the second component 1514 will not be pulled in the direction 1534. Accordingly, the arrangement of the actuator system 1500 enables the first component 1502 to move in the direction 1534 first and then after a delay (during which the pin 1518 traverses the length of the slot 1516) the second component 1514 may be moved in the direction 1534.

In an initial position, the first and second components 1502 and 1514, respectively, may be adjacent to one another and can seal off the pump chamber component 1526 from the inlet 1528 and the outlet 1530. Fluid from a reservoir or another source (not shown) may enter the pump chamber component 1526. When activated, the actuator system 1500 can first move the first component 1502 to open the inlet port 1528 to the pump chamber component 1526. After the delay, the second component 1514 may begin to move while maintaining a constant volume of space between the first and second components 1502 and 1514. The first component 1502 can move further to open the pump chamber component 1526 to the outlet 1530 after the second component 1514 has moved far enough to seal off the inlet port 1528. The movement of the first component 1502 can then stop and the second component 1514 can continue to move, thereby expelling any liquid drug in the pump chamber component 1526 out through the outlet 1530.

After the liquid drug has been expelled, the wires 1512 and 1520, respectively, may be relaxed. The first spring 1508 can cause the first component 1502 to move in a direction 1538 (e.g., opposite to the direction 1534). An extension 1540 on the first component 1502 can cause the bar 1504 to rotate back down and to re-engage the first component 1502. The first component 1502 can move in the direction 1538 until the bar meets a stop 1542.

Similarly, the second spring 1524 can cause the second component 1514 to move in the direction 1538. The second component 1514 can move in the direction 1538 until the second component 1514 meets a stop 1544. When the first and second components 1502 and 1514 have moved all the way to the right in the direction 1538, then the actuator system 1500 is reset to await activation to implement another cycle of operations. Accordingly, the actuator system 1500 can provide the movement of the components as described in relation to FIG. 13.

Figure 16:
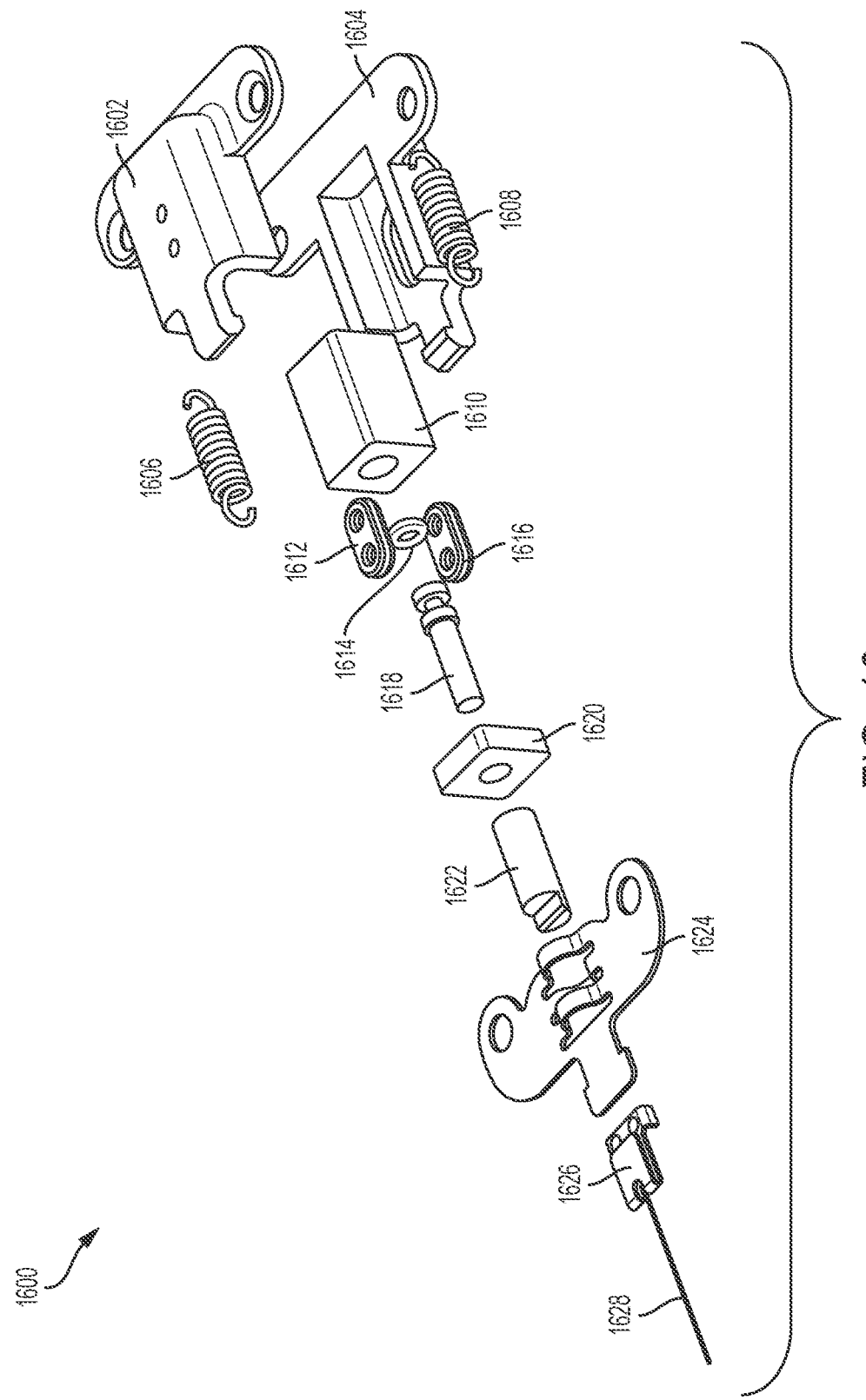
FIG. 16 illustrates an exploded view of an example of a linear volume shuttle fluid pump according to examples shown herein.

FIG. 16 illustrates an exploded view of an example of a linear volume shuttle fluid pump. As shown in FIG. 16, the linear volume shuttle fluid pump 1600 can include a two-piece guide formed by a first (or upper) guide component 1602 and a second (or lower) guide component 1604. The first and second guide components 1602 and 1604, respectively, may be formed by laser weld and/or may snap fit together. The linear volume shuttle fluid pump 1600 may further include a first spring 1606 and a second spring 1608. The linear volume shuttle fluid pump 1600 can also include a pump chamber component 1610, a first valve seal 1612, a second valve seal 1616, and a piston seal 1614. The pump chamber component 1610 may be formed from injection molded plastic or compression molding rubber. The first and second valve seals 1612 and 1616, respectively, and the piston seal 1614 may be formed from injection molded liquid silicone rubber (LSR), or the like.

As further shown in FIG. 16, the linear volume shuttle fluid pump 1600 can also include a piston 1618, a chamber cap 1620, a piston nut 1622, and a piston crimp 1624. The piston 1618 may be formed by a lathe with threads formed after by rolling. The chamber cap 1620 may be formed from injection molded plastic with ultrasonic welding or laser welding to the pump chamber component 1610. In an example, the piston nut 1622 may be formed by turned and threaded metal. In addition, the piston nut 1622 may be threaded to the piston 1618 to set a stroke of the linear volume shuttle fluid pump 1600. The stroke determining an amount of drug to be delivered or fluid to be expelled by the linear volume shuttle fluid pump 1600. The piston crimp 1624 may be formed from stamped metal and may be crimped to the piston nut 1622.

Lastly, the linear volume shuttle fluid pump 1600 can include a wire crimp 1626 and a SMA wire 1628. The wire crimp 1626 may be laser welded to the piston crimp 1624. In various examples, the piston nut 1622 may be threaded to form a gap of approximately 0.800 mm between the piston nut 1622 and the chamber cap 1620.

FIGS. 17-20 illustrate operation of the linear volume shuttle fluid pump in the example of FIG. 16. In particular, FIGS. 17-20 illustrate a sequence of operational states of the linear volume shuttle fluid pump 1600 for drawing in a portion of a liquid drug and expelling it for delivery to a patient. FIGS. 17-20 show cross-sectional views of the linear volume shuttle fluid pump 1600. The springs 1606 and 1608 may be coupled to the piston crimp 1624 and the guide components 1602/1604 in a manner that obscures their view/representation as shown in FIGS. 17-20.

Figure 17:
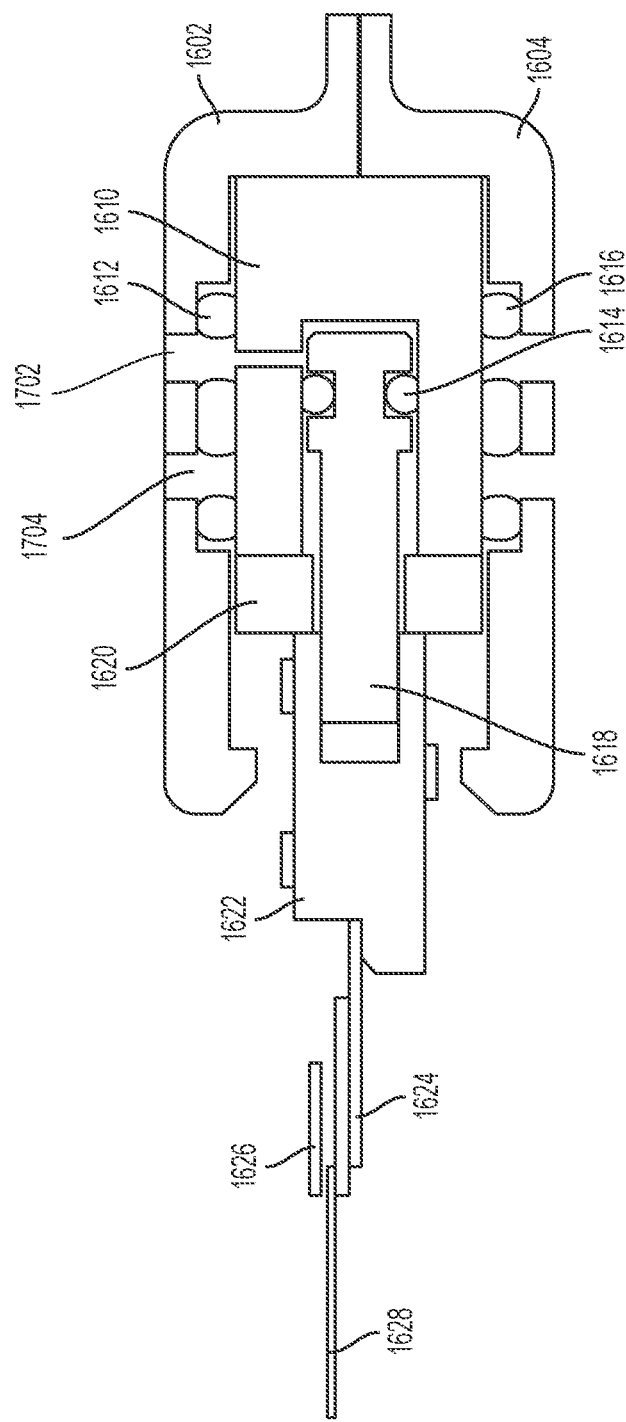
FIGS. 17-20 illustrate examples of operations of the linear volume shuttle fluid pump shown in the example of FIG. 16.

FIG. 17 illustrates the linear volume shuttle fluid pump 1600 in an initial operational state (e.g., a home position). As shown in FIG. 17, linear volume shuttle fluid pump 1600 can include an inlet 1702 and an outlet 1704. The inlet 1702 may be aligned with an opening within the pump chamber component 1610. Further, FIG. 17 shows the piston crimp 1624 coupled to the piston nut 1622 which is coupled to the piston 1618.

Figure 18:
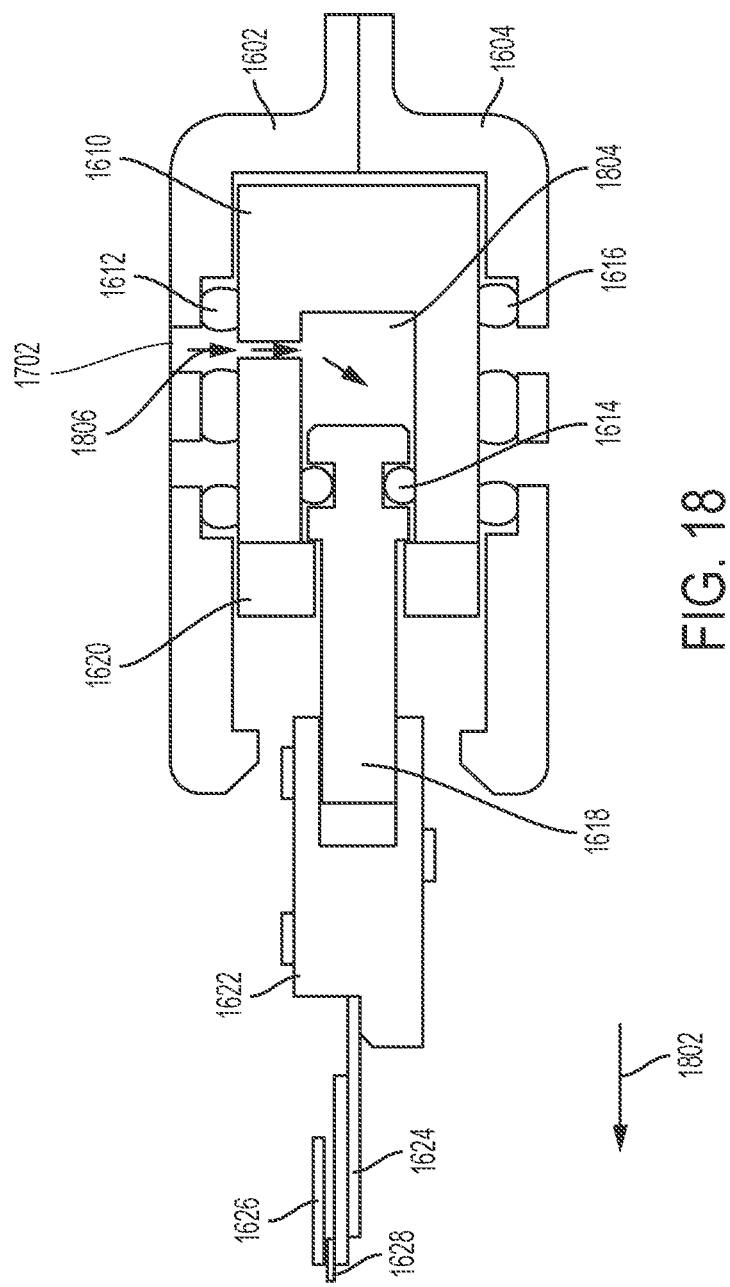

FIG. 18 illustrates the linear volume shuttle fluid pump 1600 in a subsequent state of operation relative to the state of operation shown in FIG. 17. As shown in FIG. 18, the SMA wire 1628 may be activated. When activated, the SMA wire 1628 can pull the piston 1618 (as well as the piston nut 1622) in a direction 1802. This movement opens a space 1804 for a portion of a liquid drug to flow into from the inlet 1702 (as indicated by the flow arrows 1806).

Figure 19:
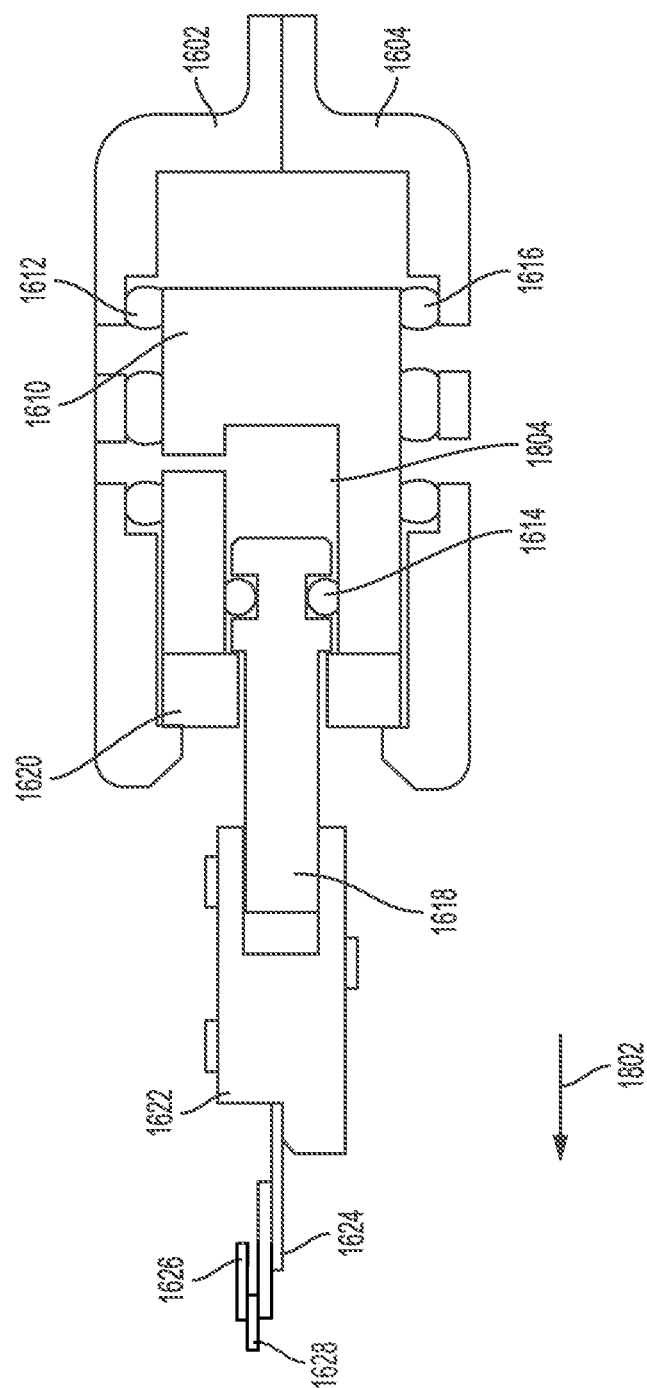

FIG. 19 illustrates the linear volume shuttle fluid pump 1600 in a subsequent state of operation relative to the state of operation shown in FIG. 18. As shown in FIG. 19, the SMA wire 1628 continues to pull the piston 1618 in the direction 1802. The piston 1618 subsequently engages the wall of the pump chamber component 1610, causing the pump chamber component 1610 and the chamber cap 1620 to also be moved in the direction 1802. This movement causes the pump chamber component 1610 to seal off the inlet 1702. Further, this movement causes the space 1804 containing liquid drug to be opened or coupled to the outlet 1704.

Figure 20:
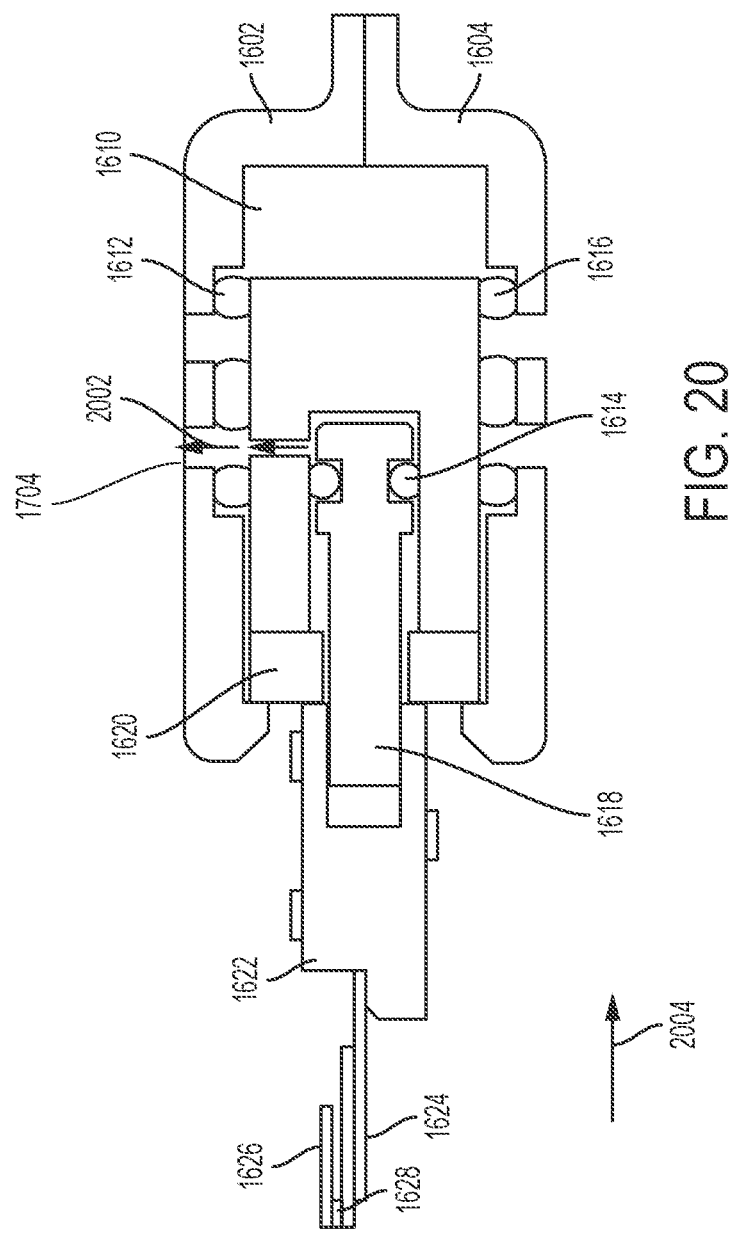

FIG. 20 illustrates the linear volume shuttle fluid pump 1600 in a subsequent state of operation relative to the state of the operation shown in FIG. 19. As shown in FIG. 20, the SMA wire 1628 may be deactivated. As a result, the springs 1606 and 1608 can pull the piston 1618 in the direction 2004. This movement causes the piston 1618 to expel the liquid drug out of the space 1804 through the outlet 1704 (as indicated by directional arrows 2002). The springs 1606 and 1608 can then further pull the piston 1618, the pump chamber component 1610, and the piston nut 1622 (as well as other components) back in the direction indicated by directional arrows 2002. As a result, the linear volume shuttle fluid pump 1600 may be reset by returning to the operational state shown in FIG. 17 to await another cycle activation.

The systems, apparatuses, and methods disclosed herein may be used to extract a portion of a liquid drug or other fluid from a reservoir without the need for a plunger. The linear volume shuttle fluid pump 100, the linear shuttle pump 1200, and linear volume shuttle fluid pump 1600 can each be considered a drive system and/or pump system for providing a stored liquid drug to a user by, for example, extracting a liquid drug from a reservoir, temporarily storing the extracted liquid drug within the pump system, and then expelling the liquid drug from the pump system for delivery to the patient. Each of the disclosed pump systems may be part of a wearable medical device such as, for example, a wearable insulin delivery device.

Certain examples of the present invention were described above. It is, however, expressly noted that the present invention is not limited to those examples, but rather the intention is that additions and modifications to what was expressly described herein are also included within the scope of the invention. Moreover, it is to be understood that the features of the various examples described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example to streamline the disclosure. This method of disclosure is not to be interpreted as reflecting an intention that the claimed examples require more features than are expressly recited in each claim. Rather, as the following claims reflect, novel subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

The invention claimed is:

1. A linear volume shuttle fluid pump, comprising:
a pump chamber component;
a piston positioned within the pump chamber component;
a chamber cap coupled to an end of the pump chamber component and positioned around the piston;
a piston crimp coupled to the piston;
a wire crimp coupled to the piston crimp; and
a shape memory alloy (SMA) wire coupled to the wire crimp.

2. The linear volume shuttle pump of claim 1, further comprising:
a guide component, wherein the pump chamber component is positioned within the guide component.

3. The linear volume shuttle pump of claim 2, wherein the guide component includes a first guide component and a second guide component coupled to one another.

4. The linear volume shuttle pump of claim 1, further comprising:
a piston nut disposed between the piston and the piston crimp.

5. The linear volume shuttle pump of claim 1, wherein the SMA wire, when activated, is configured to pull the piston in a first direction toward the chamber cap to enable a liquid drug to enter a created space formed between the piston and the pump chamber component.

6. The linear volume shuttle pump of claim 5, wherein the liquid drug enters the created space from an opening in the pump chamber component.

7. The linear volume shuttle pump of claim 6, wherein the SMA wire is operable to further pull the chamber cap, the piston, and the pump chamber component in the first direction to couple the created space to an outlet positioned in a guide component and to seal off an inlet positioned in the guide component, wherein the inlet is fluidly coupled to the opening in the pump chamber component.

8. The linear volume shuttle pump of claim 7, wherein the inlet is coupled to a reservoir storing the liquid drug and the outlet is coupled to deliver the liquid drug.

9. The linear volume shuttle pump of claim 5, wherein, when the SMA wire is deactivated, one or more springs are configured to pull the piston in a second direction, opposite to the first direction, to force the piston against the pump chamber component, thereby expelling the liquid drug out of the created space through an outlet positioned in a guide component.

10. The linear volume shuttle pump of claim 1, further comprising:
one or more springs; and
a guide component, wherein the one or more springs are coupled to the piston crimp and to one or more points on the guide component.

11. A linear volume shuttle pump, comprising:
a guide component operable to pass a liquid drug;
a pump chamber component positioned with the guide component, wherein the pump chamber includes one or more openings;
a piston positioned within the pump chamber component;
a chamber cap coupled to an end of the pump chamber component and positioned around the piston;
a piston crimp coupled to the piston;
a wire crimp coupled to the piston crimp; and
a shape memory alloy (SMA) wire coupled to the wire crimp and operable to be activated and deactivated, wherein the SMA wire, when activated, is operable to:
pull the piston in a first direction toward the chamber cap to enable the liquid drug to enter a space created by the pulling of the piston in the first direction, wherein the created space is formed between the piston and the pump chamber component.

12. The linear volume shuttle pump of claim 11, wherein the liquid drug enters the created space from an opening in the pump chamber component and from the guide component.

13. The linear volume shuttle pump of claim 11, wherein the SMA wire, when activated, is operable to further pull the chamber cap, the piston, and the pump chamber component in the first direction to couple the created space to an outlet positioned in the guide component and to seal off an inlet positioned in a guide component, wherein the inlet is fluidly coupled to the opening in the pump chamber component.

14. The linear volume shuttle pump of claim 13, wherein the outlet of the guide component is operable to enable expelling of a liquid drug out of the linear volume shuttle pump.

15. The linear volume shuttle pump of claim 11, wherein, when the SMA wire is deactivated, one or more springs are configured to pull the piston in a second direction, opposite to the first direction, to press the piston against the pump chamber component, thereby expelling the liquid drug out of the created space through an outlet positioned in a guide component.

16. The linear volume shuttle pump of claim 11, further comprising:
   a spring having a first end and a second end, wherein the first end of the spring is coupled to the guide component and the second end of the spring is coupled to the wire crimp, and the spring, when the SMA wire is deactivated, is operable to:
   pull the piston in a second direction, opposite to the first direction, to press the piston against the pump chamber component, thereby expelling the liquid drug out of the created space through an outlet positioned in the guide component.

17. The linear volume shuttle pump of claim 16, wherein the spring is further operable to:
   pull the piston and the pump chamber component further back into the guide component to a position where the one or more openings is positioned to be fluidly coupled to an inlet positioned in a guide component.

18. The linear volume shuttle pump of claim 11, further comprising:
   a piston nut disposed between the piston and the piston crimp, wherein the piston nut is operable to be attached to the piston.

19. The linear volume shuttle pump of claim 18, wherein the piston nut is operable to set a stroke of the linear volume shuttle fluid pump, and the setting of the stroke determines an amount of liquid drug to be expelled from the pump chamber component.

20. The linear volume shuttle pump of claim 11, wherein the guide component further comprises an open end operable to engage the chamber cap and thereby stopping movement of the pump chamber component.

* * * * *